US011880485B2

(12) United States Patent
Takagi et al.

(10) Patent No.: US 11,880,485 B2
(45) Date of Patent: Jan. 23, 2024

(54) MEDICAL INFORMATION ANONYMIZING SYSTEM AND ANONYMIZING METHOD SETTING DEVICE

(71) Applicant: Canon Medical Systems Corporation, Otawara (JP)

(72) Inventors: Shingo Takagi, Otawara (JP); Kei Yamaji, Nasushiobara (JP); Shinichi Nakano, Utsunomiya (JP); Hideki Tada, Nasushiobara (JP); Satoshi Okuyama, Nasushiobara (JP); Hidetoshi Ishigami, Otawara (JP); Seiji Mikami, Otawara (JP); Norimasa Muroi, Nasushiobara (JP); Hiroshi Kurosawa, Nasushiobara (JP); Takumi Kaneko, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 250 days.

(21) Appl. No.: 16/718,456

(22) Filed: Dec. 18, 2019

(65) Prior Publication Data

US 2020/0226282 A1    Jul. 16, 2020

(30) Foreign Application Priority Data

Dec. 19, 2018  (JP) ................................ 2018-237739
Dec. 17, 2019  (JP) ................................ 2019-227533

(51) Int. Cl.
*G06F 21/62*  (2013.01)
*G16H 30/20*  (2018.01)
(Continued)

(52) U.S. Cl.
CPC ...... *G06F 21/6245* (2013.01); *G06F 21/6254* (2013.01); *G16H 10/60* (2018.01); *G16H 30/20* (2018.01); *H04L 63/0421* (2013.01)

(58) Field of Classification Search
CPC ...... G06F 21/60; G06F 21/62; G06F 21/6245; G06F 21/6254; G16H 30/00; G16H 30/20;
(Continued)

(56) References Cited

U.S. PATENT DOCUMENTS 9,390,153 B1 * 7/2016 Tochilnik ............... G16H 40/20
2012/0046972 A1 * 2/2012 Tonti .................... G16H 40/67
                                                                705/3

(Continued)

FOREIGN PATENT DOCUMENTS

JP    2006-330832 A    12/2006
JP    2015-125515 A     7/2015
(Continued)

OTHER PUBLICATIONS

Notification of Reasons for Refusal dated Sep. 5, 2023, issued in corresponding Japanese patent application No. 2019-227533.

*Primary Examiner* — D'Arcy Winston Straub
(74) *Attorney, Agent, or Firm* — Oblon, McClelland, Maier & Neustadt, L.L.P.

(57) ABSTRACT

A medical information anonymizing system includes a processing circuitry. The processing circuitry acquires medical information generated in a format based on a communication standard for a medical image and including a medical image and supplementary information. The processing circuitry adds the anonymization reference information indicating an anonymizing method for anonymizing the medical information to the supplementary information in the medical information. The processing circuitry configured to receive the medical information in which the anonymization reference information is added to the supplementary information and, based on the anonymization reference information added to the medical information, anonymize at least one of (Continued)

the medical image and the supplementary information included in the medical information.

14 Claims, 21 Drawing Sheets

(51) Int. Cl.
  *G16H 10/60* (2018.01)
  *H04L 9/40* (2022.01)
(58) Field of Classification Search
  CPC ..... G16H 10/60; H04L 63/0421; H04L 63/04; H04L 63/0407
  See application file for complete search history.

(56) References Cited

U.S. PATENT DOCUMENTS

| | | |
|---|---|---|
| 2013/0208966 A1 | 8/2013 | Zhao et al. |
| 2013/0279596 A1 | 10/2013 | Gisquet et al. |
| 2013/0287112 A1 | 10/2013 | Gisquet et al. |
| 2013/0287113 A1 | 10/2013 | Gisquet et al. |
| 2013/0294521 A1 | 11/2013 | Gisquet et al. |
| 2016/0267227 A1* | 9/2016 | Takeyama ............... G16Z 99/00 |
| 2016/0277744 A1 | 9/2016 | Gisquet et al. |
| 2017/0032084 A1* | 2/2017 | Stalling ................. G16H 30/40 |
| 2017/0091391 A1* | 3/2017 | LePendu ............. G06F 21/6245 |
| 2017/0372096 A1* | 12/2017 | Yousfi .................... G16H 10/60 |
| 2018/0082020 A1* | 3/2018 | Rajagopal .............. G16H 10/60 |
| 2018/0241999 A1 | 8/2018 | Gisquet et al. |
| 2018/0242000 A1 | 8/2018 | Gisquet et al. |
| 2018/0242001 A1 | 8/2018 | Gisquet et al. |
| 2018/0316921 A1 | 11/2018 | Gisquet et al. |
| 2018/0352236 A1 | 12/2018 | Gisquet et al. |
| 2019/0098313 A1 | 3/2019 | Gisquet et al. |
| 2019/0098314 A1 | 3/2019 | Gisquet et al. |
| 2019/0098315 A1 | 3/2019 | Gisquet et al. |

FOREIGN PATENT DOCUMENTS

| | | |
|---|---|---|
| JP | 2017-138991 A | 8/2017 |
| JP | 2018-026826 A | 2/2018 |
| WO | 2012/017612 A1 | 2/2012 |

* cited by examiner

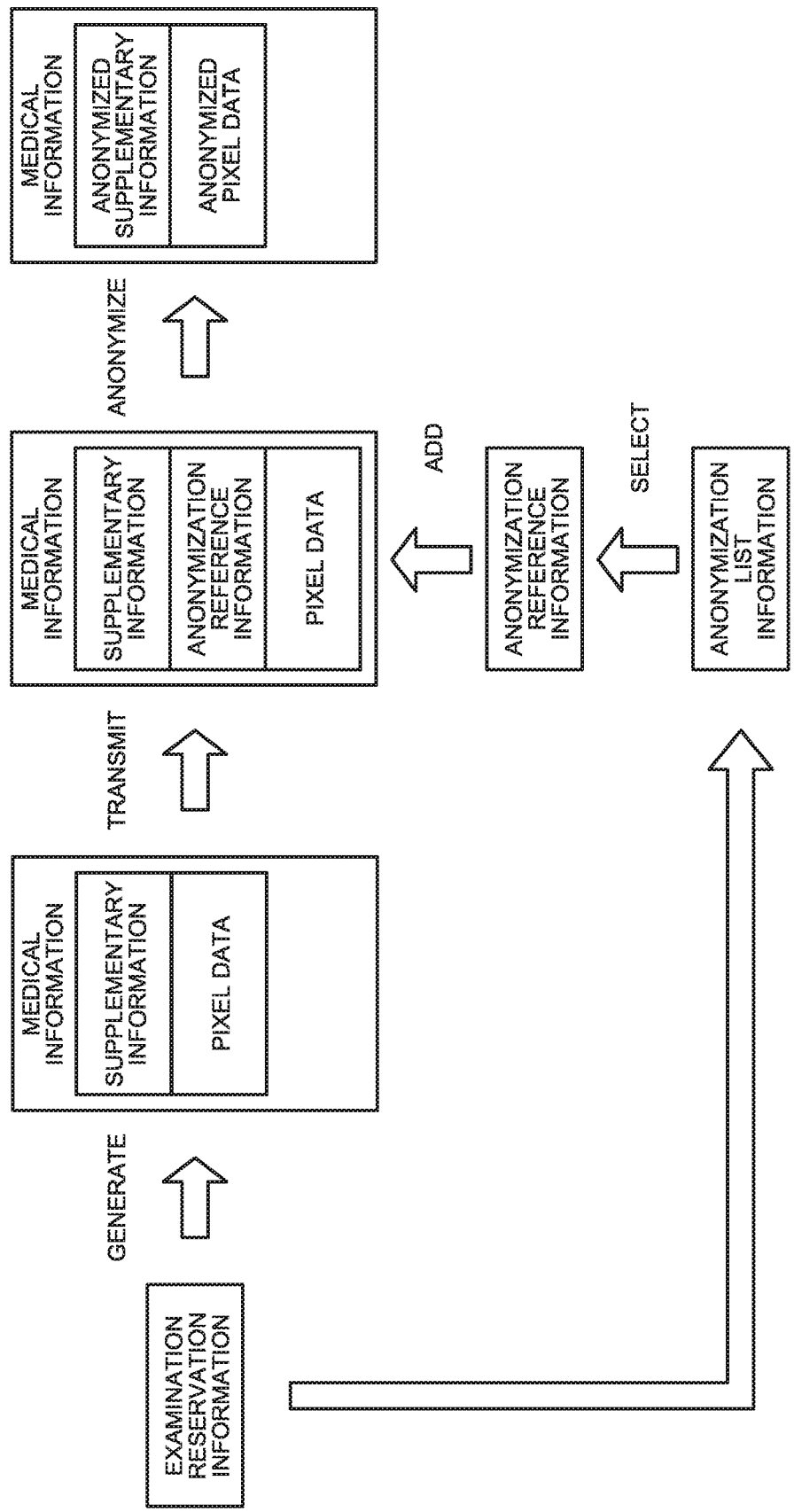

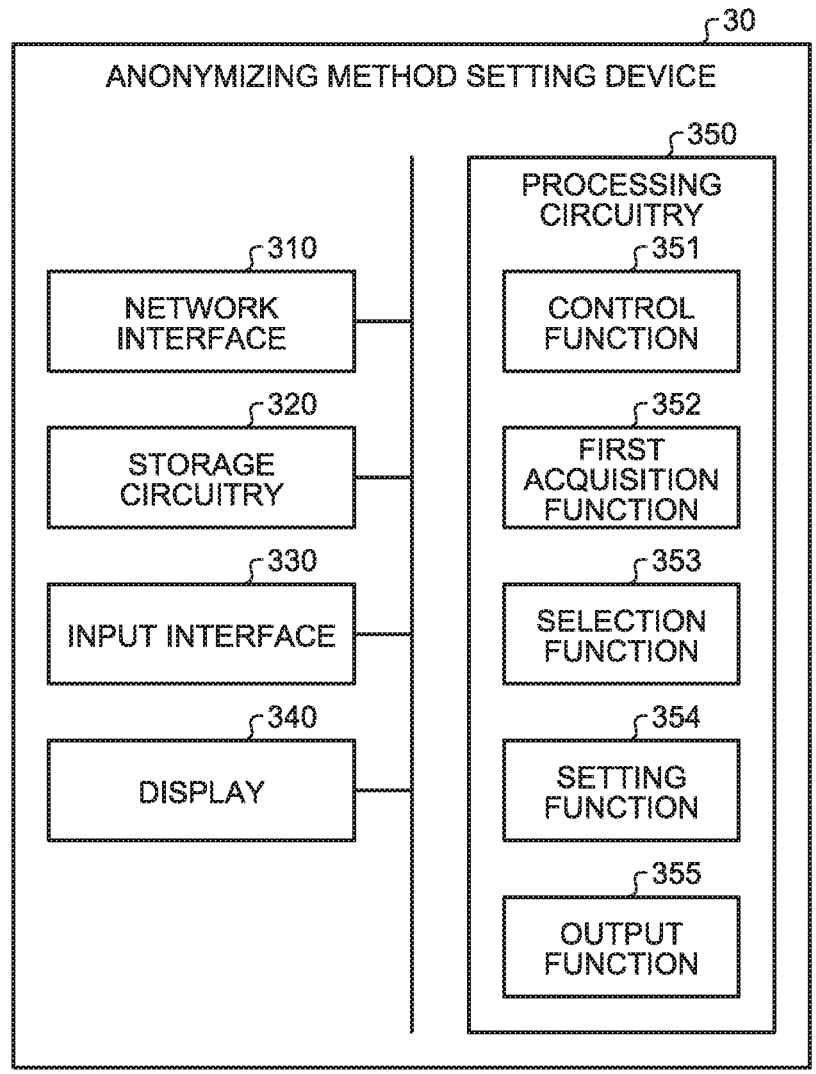

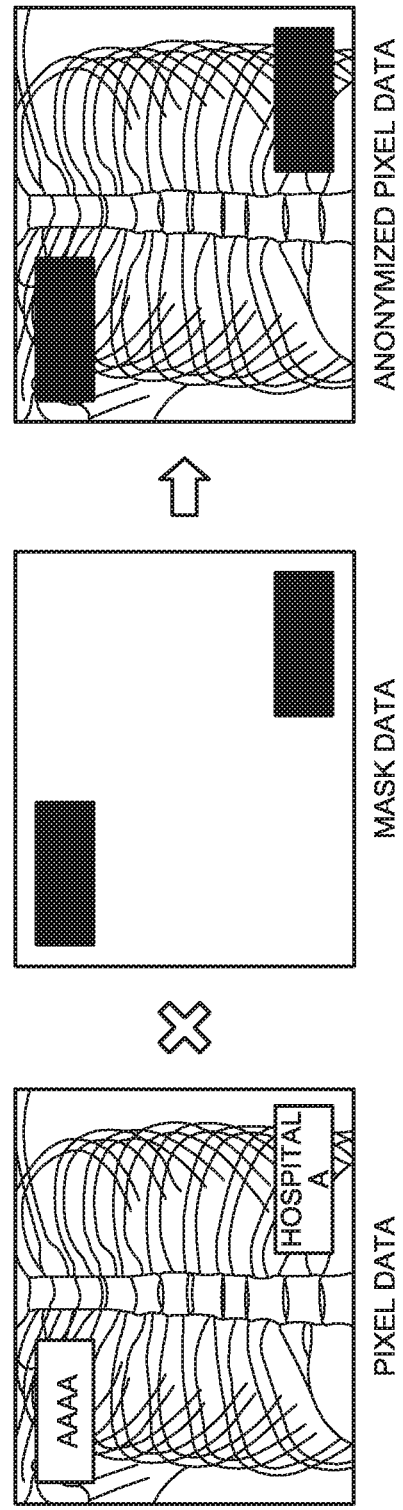

FIG.7

| TAG | ATTRIBUTE |
|---|---|
| ⋮ | ⋮ |
| (7317, 1010) | RESEARCH SITE A/ DISEASE RESEARCH |
| (7317, 1020) | (0010, 0010) D: 13;<br>(0010, 0020) D: %LID;<br>(0010, 0030) X;<br>(7FE0, 0010) MASK DATA; |
| ⋮ | ⋮ |

SUPPLE-MENTARY INFORMATION

PIXEL DATA

FIG.8

ANONYMIZATION SPECIFICATION DIALOGUE

THIS ITEM IS ANONYMIZATION TARGET. PLEASE DELETE PART CORRESPONDING TO PERSONAL INFORMATION OR INPUT IT SANDWICHED BETWEEN PARENTHESES.

MR. [AAAA] HAD A PROBLEM IN LIVER FUNCTION BEFORE AND IS UNDER TREATMENT IN OUR HOSPITAL.

FIG.13

| ANONYMIZING METHOD | ANONYMIZING STRENGTH |
|---|---|
| D (REPLACE) | 10 |
| Z (ZEROFILL) | 20 |
| X (DELETE) | 100 |
| N (NONE) | 0 |
| C (OPERATOR'S OPERATION) | 5 |
| U (REPLACE WITH UID) | 25 |
| ⋮ | ⋮ |

FIG.14

<ANONYMIZATION REFERENCE INFORMATION IN ANONYMIZATION LIST INFORMATION>

| TAG | ATTRIBUTE |
|---|---|
| 0010, 0010 | D; 13 (REPLACE) |
| 0010, 0020 | X (DELETE) |
| ⋮ | ⋮ |

<ANONYMIZATION REFERENCE INFORMATION OF RECIPIENT>

| TAG | ATTRIBUTE |
|---|---|
| 0010, 0010 | N (NO ANONYMIZATION) |
| 0010, 0020 | D; 24 (REPLACE) |
| ⋮ | ⋮ |

| TAG | ATTRIBUTE |
|---|---|
| 0010, 0010 | D; 13 |
| 0010, 0020 | X (DELETE) |
| ⋮ | ⋮ |

MEDICAL INFORMATION ANONYMIZING SYSTEM AND ANONYMIZING METHOD SETTING DEVICE

CROSS-REFERENCE TO RELATED APPLICATIONS

This application is based upon and claims the benefit of priority from Japanese Patent Application No. 2018-237739, filed on Dec. 19, 2018 and No. 2019-227533, filed on Dec. 17, 2019; the entire contents of which are incorporated herein by reference.

FIELD

Embodiments described herein relate generally to a medical information anonymizing system and an anonymizing method setting device.

BACKGROUND

Conventionally, a medical institution such as a hospital has the task to provide the medical information on the subject, such as the image data captured by a medical image diagnostic device, to a research institution, or the like, which performs a joint research. In order to prevent the leakage of personal information on the subject, the medical institution, which is a sender, anonymizes the medical information.

BRIEF DESCRIPTION OF THE DRAWINGS

FIG. 3 is a diagram illustrating an example of the procedure of anonymization according to the first embodiment;

FIG. 4 is a block diagram illustrating an example of the configuration of an anonymizing method setting device according to the first embodiment;

FIG. 5 is an explanatory diagram illustrating an example of anonymization list information;

FIG. 6 is a diagram illustrating an example of a process to mask pixel data with mask data;

FIG. 7 is a diagram illustrating an example of the setting of recipient information and anonymization reference information;

FIG. 8 is a diagram illustrating an example of an anonymization specification screen;

FIG. 13 is a diagram illustrating an example of anonymization strength information;

FIG. 14 is a diagram illustrating an example of the selection of anonymization reference information;

DETAILED DESCRIPTION

A medical information anonymizing system according to an embodiment includes a processing circuitry. The processing circuitry acquires medical information generated in a format based on a communication standard for a medical image and including a medical image and supplementary information. The processing circuitry adds the anonymization reference information indicating an anonymizing method for anonymizing the medical information to the supplementary information in the medical information. The processing circuitry configured to receive the medical information in which the anonymization reference information is added to the supplementary information and, based on the anonymization reference information added to the medical information, anonymize at least one of the medical image and the supplementary information included in the medical information.

An anonymizing method setting device according to an embodiment includes a processing circuitry. The processing circuitry acquires the medical information generated in a format based on a communication standard for a medical image and including a medical image and supplementary information. The processing circuitry configured to add the anonymization reference information indicating an anonymizing method for anonymizing the medical information to the supplementary information in the medical information.

An embodiment of a medical information anonymizing system and an anonymizing method setting device is described below with reference to the drawings. The details described in one embodiment or modification may be similarly applied to other embodiments or modifications.

First Embodiment

Figure 1:
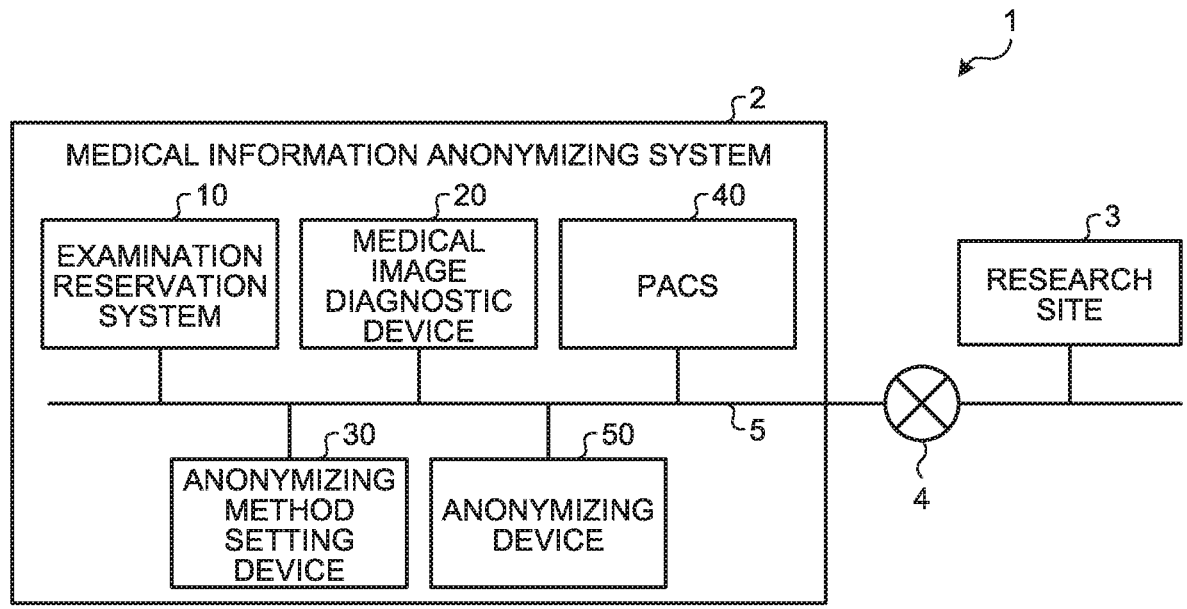
FIG. 1 is a diagram illustrating an example of the configuration of a medical information processing system according to a first embodiment.

A first embodiment is described. FIG. 1 is a diagram illustrating an example of the configuration of a medical information processing system 1 according to the first embodiment. As illustrated in FIG. 1, the medical information processing system 1 includes a medical information anonymizing system 2 and a research site 3. The medical information anonymizing system 2 is a system installed in a medical institution, such as a hospital, to provide anonymized medical information to a recipient such as the research site 3. The medical information anonymizing system 2 is communicatively connected to the research site 3 via a first network 4 such as the Internet. The medical information anonymizing system 2 and the research site 3 perform communications in accordance with a communication protocol defined by the DICOM (Digital Imaging and Communications in Medicine) standard.

As illustrated in FIG. 1, the medical information anonymizing system 2 includes an examination reservation system 10, a medical image diagnostic device 20, an anonymizing method setting device 30, a PACS (Picture Archiving and Communication System) 40, and an anonymizing device 50. Each system and each device included in the medical information anonymizing system 2 are communicatively connected via, for example, a second network 5 installed in a hospital. Each system and each device included in the medical information anonymizing system 2 perform communications in accordance with a communication protocol defined by the DICOM standard. The configuration illustrated in FIG. 1 is merely an example, and devices other than the examination reservation system 10, the medical image diagnostic device 20, the anonymizing method setting device 30, the PACS 40, and the anonymizing device 50 illustrated in the figure may be connected to the second network 5.

The examination reservation system 10 is a system that, for example, receives reservations for examination orders and manages reservations for examinations. More specifically, the examination reservation system 10 generates examination reservation information to acquire the medical information to be provided when an operation of registering the provision of the medical information is received. The examination reservation information includes the recipient information indicating the recipient and the purpose of the recipient and the provided-content information indicating the content of the medical information to be provided. For example, the examination reservation system 10 is implemented by using a computer device such as a server or a workstation.

The medical image diagnostic device 20 captures the subject to generate medical information. More specifically, the medical image diagnostic device 20 captures the subject in accordance with the examination reservation information transmitted from the examination reservation system 10 to generate medical information. Examples of the medical image diagnostic device 20 include an X-ray diagnostic device, an X-ray CT (Computed Tomography) device, an MRI (Magnetic Resonance Imaging) device, an ultrasonic diagnostic device, a SPECT (Single Photon Emission Computed Tomography) device, and a PET (Positron Emission Computed Tomography) device.

Figure 2:
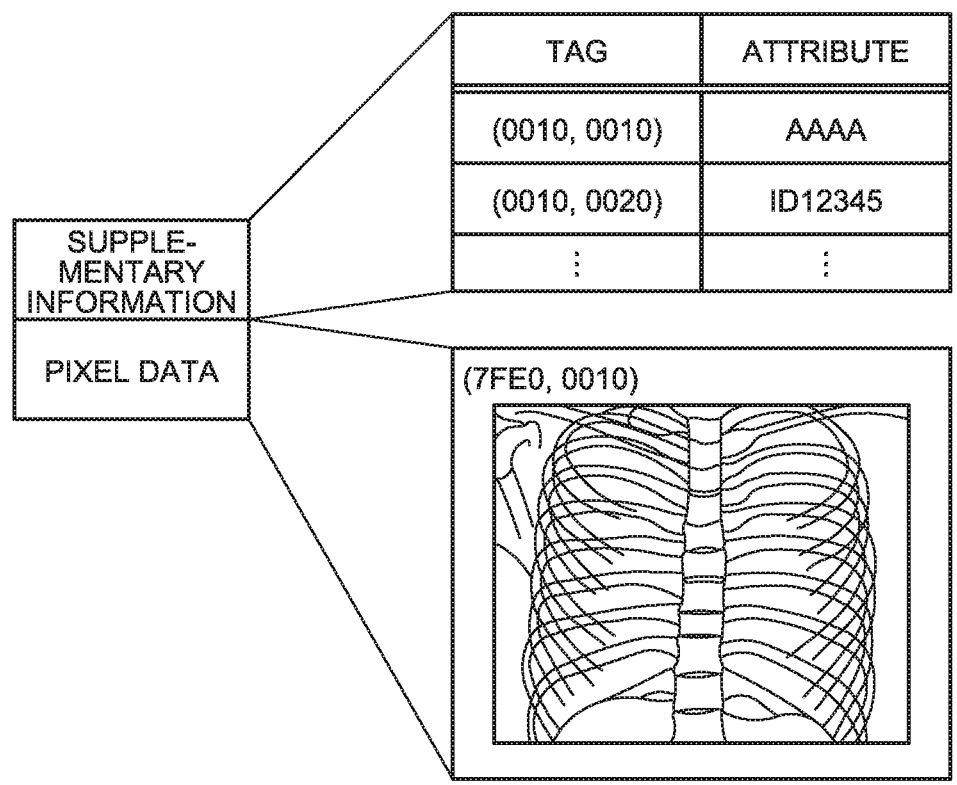
FIG. 2 is a diagram illustrating an example of medical information.

Here, the medical information is described. FIG. 2 is a diagram illustrating an example of the medical information. The medical information is generated in, for example, the DICOM format. The medical information includes supplementary information and pixel data. The supplementary information is the information indicating an attribute of the medical information. In the supplementary information, an attribute is related to each tag. The attribute is the information indicating the content of the medical information. For example, the patient's name is related to the tag (0010, 0010). For example, the patient identifier with which a patient may be identified is related to the tag (0010, 0020). The pixel data includes image data generated when the medical image diagnostic device 20 captures the subject. Image data is related to the tag (7FE0, 0010).

With reference back to FIG. 1, the anonymizing method setting device 30 sets the method for anonymizing medical information. More specifically, the anonymizing method setting device 30 selects the anonymization reference information indicating the method for anonymizing the medical information in accordance with the recipient information included in the examination reservation information transmitted from the examination reservation system 10. The anonymizing method setting device 30 adds the selected anonymization reference information to the medical information generated by the medical image diagnostic device 20 based on the examination reservation information. For example, the anonymizing method setting device 30 is implemented by using a computer device such as a server or a workstation.

The PACS 40 stores the medical information generated by the medical image diagnostic device 20 and the medical information to which anonymization reference information has been added by the anonymizing method setting device 30. More specifically, the PACS 40 receives medical information from the medical image diagnostic device 20 or the anonymizing method setting device 30. The PACS 40 stores and manages the received medical image in a storage circuitry, or the like, of its own. When receiving the medical information to which the anonymization reference information is added, the PACS 40 transmits the medical information to the anonymizing device 50. For example, the PACS 40 is implemented by using a computer device such as a server or a workstation.

The anonymizing device 50 anonymizes medical information. The anonymizing device 50 executes an anonymization process to hide the personal information included in the medical information based on the anonymization reference information added to the medical information. The anonymizing device 50 transmits the anonymized medical information to the research site 3. For example, the anonymizing device 50 is implemented by using a computer device such as a server or a workstation.

The research site 3 is provided in, for example, a research institution that has a relationship for joint research with the medical institution of the medical information anonymizing system 2 to receive medical information provided by the medical information anonymizing system 2. For example, the research site 3 is implemented by using a computer device such as a server or a workstation.

The outline of the process to anonymize medical information in the medical information anonymizing system 2 according to the first embodiment is described.

Here, FIG. 3 is a diagram illustrating an example of the procedure of anonymization according to the first embodiment. The examination reservation system 10 generates examination reservation information when the examination reservation by the medical image diagnostic device 20 is received. The examination reservation information includes the recipient of the medical information and the recipient's usage purpose of the medical information. The medical image diagnostic device 20 generates the medical information on the subject based on the examination reservation information. The anonymizing method setting device 30 selects anonymization reference information from the anonymization list information in which the anonymization reference information is related to the recipient information indicating the recipient of the medical information and the recipient's usage purpose of the medical information. The anonymizing method setting device 30 adds the selected anonymization reference information to the medical information generated by the medical image diagnostic device 20. The anonymizing device 50 generates the medical information in which the supplementary information and the pixel data are anonymized based on the anonymization reference information added to the medical information.

Next, the configuration of the anonymizing method setting device 30 according to the first embodiment is described.

FIG. 4 is a block diagram illustrating an example of the configuration of the anonymizing method setting device 30 according to the first embodiment. As illustrated in FIG. 4, the anonymizing method setting device 30 according to the first embodiment includes a network interface 310, a storage circuitry 320, an input interface 330, a display 340, and a processing circuitry 350.

The network interface 310 is connected to the processing circuitry 350 and controls the transmission of various types of data and communications performed with the examination reservation system 10, the medical image diagnostic device 20, the PACS 40, and the anonymizing device 50 via the first network 4. More specifically, the network interface 310 receives various types of information from each system and outputs the received information to the processing circuitry 350. The network interface 310 is implemented by using, for example, a network card, a network adapter, or an NIC (Network Interface Controller).

The storage circuitry 320 is connected to the processing circuitry 350 and stores various types of data. The storage circuitry 320 is implemented by using, for example, a semiconductor memory device such as a RAM (random access memory) or a flash memory, a hard disk, or an optical disk. For example, the storage circuitry 320 stores the anonymization list information in which recipient information and anonymization reference information are related. That is, the storage circuitry 320 is a first storage unit in which the recipient of medical information and anonymization reference information are stored in relation to each other. The storage circuitry 320 is a second storage unit in which the usage purpose of medical information and anonymization reference information are stored in relation to each other.

FIG. 5 is an explanatory diagram illustrating an example of the anonymization list information. In the anonymization list information, recipient information and anonymization reference information are related to each other. The recipient information includes the information indicating the recipient and the information indicating the recipient's usage purpose of the medical information. The anonymization list information illustrated in FIG. 5 indicates the recipient information in which the recipient is "research site A" and the usage purpose is "disease research". The recipient information may include both or either one of the information indicating the recipient and the information indicating the recipient's usage purpose of the medical information. The anonymization reference information includes the information indicating the tag to be anonymized and the anonymizing method. An anonymizing method compatible with the DICOM standard is set as the anonymizing method.

In the anonymization reference information illustrated in FIG. 5, "(0010, 0010) D:13;" indicates that the attribute related to the tag "(0010, 0010)" is replaced with "13". Furthermore, "(0010, 0020) D:% LID;" indicates that the attribute related to the tag "(0010, 0020)" is replaced with the hash value calculated by a hash function. In this case, the attribute before the replacement may be calculated from the hash value. Further, "(0010, 0030) X;" indicates that the attribute related to the tag "(0010, 0020)" is to be deleted. Moreover, "(7FE0, 0010) mask data;" indicates that the pixel data related to the tag "(7FE0, 0010)" is to be masked with mask data. The mask data is the information indicating the mask location in the pixel data.

FIG. 6 is a diagram illustrating an example of the process to mask pixel data with mask data. The pixel data illustrated in FIG. 6 includes personal information such as "AAAA" indicating the name of the patient and "hospital A" indicating the name of the hospital in which the pixel data was captured. The mask data illustrated in FIG. 6 indicates the area to be masked by painting the pixel data. By combining the pixel data and the mask data, anonymized pixel data in which the personal information is anonymized is generated.

A program compatible with the DICOM standard may be set as the anonymizing method in the anonymization reference information. For example, a program for replacement with the identifier corresponding to the patient identifier may be set. Thus, a plurality of sets of medical information is anonymized such that the sets of medical information belong to the same person. The program may include a state variable, an ID (identification), an algorithm, a time, and the like.

With reference back to FIG. 4, the input interface 330 converts the input operation received from the operator into an electric signal and outputs the electric signal to the processing circuitry 350. The input interface 330 is implemented by using an input device such as a trackball, a switch button, a mouse, a keyboard, a touchpad for performing an input operation due to the touch with an operation surface, a touch screen in which a display screen and a touchpad are integrated, a non-contact input interface using an optical sensor, or a sound input interface. The input interface 330 may be a control circuitry for a connection interface, or the like, which receives an electronic signal corresponding to an operation from an operation device provided separately from the anonymizing method setting device 30.

The display 340 presents various types of information and various images output from the processing circuitry 350. For example, the display 340 is implemented by using a display device such as an organic EL (electro luminescence) monitor, a liquid crystal monitor, a CRT (cathode ray tube) monitor, or a touch panel. For example, the display 340 presents a GUI (graphical user interface) for receiving the operator's instruction, various types of display image data, and various processing results by the processing circuitry 350.

The processing circuitry 350 controls each component included in the anonymizing method setting device 30. For example, the processing circuitry 350 is implemented by using a processor. More specifically, the processing circuitry 350 according to the first embodiment includes a control function 351, a first acquisition function 352, a selection function 353, a setting function 354, and an output function 355.

For example, each of the processing functions executed by the control function 351, the first acquisition function 352, the selection function 353, the setting function 354, and the output function 355, which are components of the processing circuitry 350 illustrated in FIG. 4, is stored in the storage circuitry 320 in the form of a program executable by a computer. The processing circuitry 350 is a processor that reads and executes each program from the storage circuitry 320 to perform the function corresponding to each program. In other words, after having read each program, the processing circuitry 350 provides each of the functions illustrated in the processing circuitry 350 of FIG. 4.

All the processing functions, the control function 351, the first acquisition function 352, the selection function 353, the setting function 354, and the output function 355, may be recorded in the storage circuitry 320 in the form of a single program executable by a computer. For example, such a program is also referred to as an anonymization setting program. In this case, the processing circuitry 350 reads the anonymization setting program from the storage circuitry 320 and executes the read anonymization setting program to implement the control function 351, the first acquisition function 352, the selection function 353, the setting function 354, and the output function 355 corresponding the anonymization setting program.

The first acquisition function 352 is an example of a first acquiring unit. The setting function 354 is an example of an adding unit, a display control unit, and a storage control unit.

The control function 351 performs the overall control on the anonymizing method setting device 30. For example, the control function 351 controls the input interface 330 so as to receive various operations.

The first acquisition function 352 acquires medical information generated in a format based on the communication standard for a medical image and including the medical image and supplementary information. The format based on the communication standard for a medical image is, for example, the DICOM standard. That is, the first acquisition function 352 acquires the medical information generated in the format specified in the DICOM standard. More specifically, the first acquisition function 352 controls the network interface 310 so as to acquire examination reservation information and medical information generated based on the examination reservation information. The control function 351 causes the storage circuitry 320 to store the acquired examination reservation information and medical information.

The selection function 353 selects the anonymization reference information corresponding to the recipient of the medical information acquired by the first acquisition function 352 from the anonymization list information in which the recipient information indicating the recipient of the medical information is related to the anonymization reference information indicating the anonymizing method for anonymizing the medical information. When the examination reservation information includes the usage purpose of the medical information, the selection function 353 selects, from the anonymization list information, the anonymization reference information corresponding to the usage purpose of the medical information for the recipient in the medical information acquired by the first acquisition function 352.

More specifically, when the first acquisition function 352 acquires medical information, the selection function 353 extracts the recipient information from the examination reservation information related to the generation of the medical information. The selection function 353 selects anonymization reference information specified by the extracted recipient information from the anonymization list information. When the recipient information includes both the recipient and the usage purpose of the medical information, the selection function 353 selects the anonymization reference information corresponding to both of them from the anonymization list information. When the recipient information includes any one of the recipient and the usage purpose of the medical information, the selection function 353 selects the anonymization reference information corresponding to the recipient or the usage purpose included in the recipient information from the anonymization list information.

The setting function 354 adds the anonymization reference information indicating the anonymizing method for anonymizing the medical information to the supplementary information in the medical information. That is, the setting function 354 reads the anonymization reference information corresponding to the recipient of the medical information from the storage circuitry 320 and adds the anonymization reference information to the supplementary information in the medical information. The setting function 354 reads the anonymization reference information corresponding to the usage purpose of the medical information from the storage circuitry 320 and adds the anonymization reference information to the supplementary information in the medical information.

More specifically, the setting function 354 adds anonymization reference information to a private tag or a standard tag compatible with the DICOM standard. The private tag is a tag in which any value may be set in the DICOM standard. The standard tag is a tag for which the indication of the value of the tag in the DICOM standard is previously determined. Specifically, the setting function 354 sets the anonymization reference information selected by the selection function 353 in the area where any information in the medical information generated in the DICOM format may be written. The setting function 354 sets the recipient information indicating the recipient of the medical information in the area where any information in the medical information generated in the DICOM format may be written. FIG. 7 is a diagram illustrating an example of the setting of the recipient information and the anonymization reference information. The setting function 354 sets the recipient information and the anonymization reference information in the tags in which any information in the medical information generated in the DICOM format may be set. In the medical information illustrated in FIG. 7, the setting function 354 sets the recipient information in the tag (7317, 1010) and sets the anonymization reference information in the tag (7317, 1020). In the medical information illustrated in FIG. 7, one piece of recipient information and anonymization reference information are set. However, when medical information is transmitted to a plurality of recipients, the setting function 354 may set a plurality of sets of recipient information and anonymization reference information.

The setting function 354 displays an anonymization specification screen for specifying the anonymization target when the anonymizing method indicated by the anonymization reference information has a setting in which the operator specifies the anonymization target. FIG. 8 is a diagram illustrating an example of the anonymization specification screen. For example, in the DICOM format, the tag (0010, 4000) is a tag to which the operator may freely write information. Therefore, as illustrated in FIG. 8, when the operator has written a text, it is difficult to specify the anonymization target, which is the part to be anonymized. Therefore, the setting function 354 displays the anonymization specification screen illustrated in FIG. 8 to request the designation of the anonymization target. The anonymization specification screen illustrated in FIG. 8 indicates that "AAAAA" between parentheses is the anonymization target. The anonymization target is replaced with, for example, a hidden character. The setting function 354 may display the anonymization target so as to be specified by using a predetermined method as well as Parentheses. For example, it may be expressed by surrounding it with a symbol such as an asterisk.

The setting function 354 learns the anonymization target, which is to be anonymized, by machine learning. Specifically, the setting function 354 causes the storage circuitry 320, or the like, to store the anonymization target specified on the anonymization specification screen. Then, when the medical information includes the information that is identical to the anonymization target previously stored by the setting function 354, the setting function 354 causes the anonymization specification screen to be displayed, in which the information identical to the anonymization target is specified as the anonymization target. More specifically, the setting function 354 stores a character string, or the like, sandwiched between parentheses. When the anonymization specification screen includes the stored character string, the setting function 354 displays the corresponding character string sandwiched between parentheses. The anonymization target is not limited to a character string but may be image data, etc.

After the setting function 354 sets the recipient information and the anonymization reference information in the medical information, the output function 355 transmits (outputs) the medical information to the PACS 40. More specifically, the output function 355 controls the network interface 310 so as to transmit output) the medical information to the PACS 40. Thus, the PACS 40 stores the medical information in which the recipient information and the anonymization reference information are set.

Figure 9:
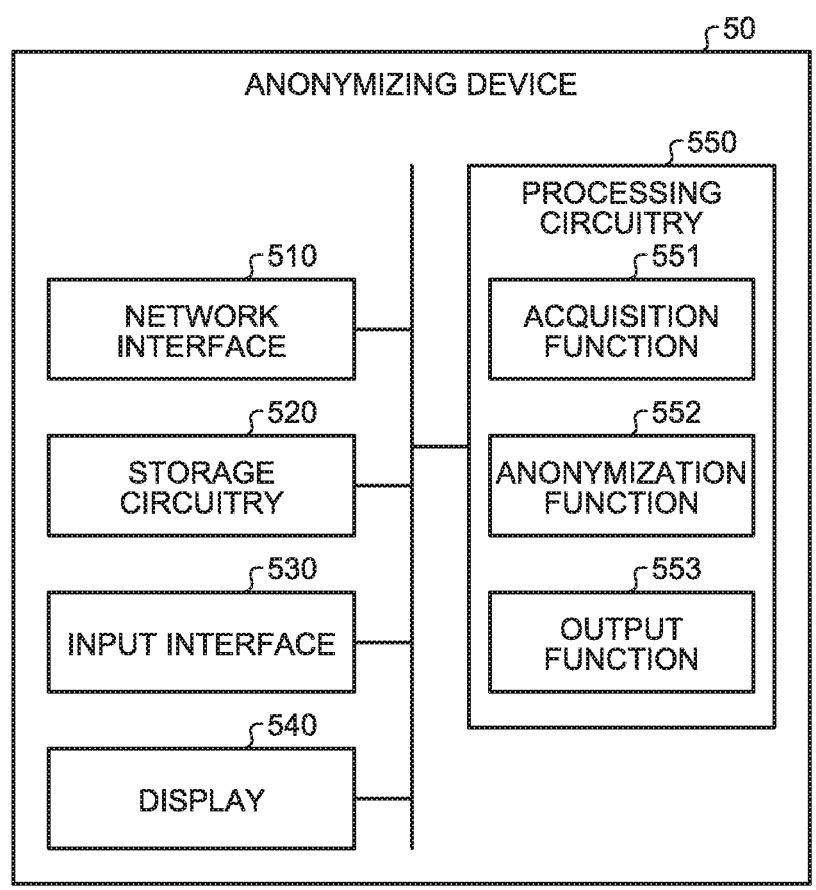
FIG. 9 is a block diagram illustrating an example of the configuration of an anonymizing device according to the first embodiment.

FIG. 9 is a block diagram illustrating an example of the configuration of the anonymizing device 50 according to the first embodiment. As illustrated in FIG. 9, the anonymizing device 50 according to the first embodiment includes a network interface 510, a storage circuitry 520, an input interface 530, a display 540, and a processing circuitry 550.

The network interface 510 is connected to the processing circuitry 550 and controls the transmission of various types of data and communications performed with the examination reservation system 10, the medical image diagnostic device 20, the anonymizing method setting device 30, and the PACS 40 via the first network 4. Specifically, the network interface 510 receives various types of information from each system and outputs the received information to the processing circuitry 550. The network interface 510 is implemented by using, for example, a network card, a network adapter, or an NIC.

The storage circuitry 520 is connected to the processing circuitry 550 and stores various types of data. The storage circuitry 520 is implemented by using, for example, a semiconductor memory device such as a RAM or a flash memory, a hard disk, or an optical disk.

The input interface 530 converts the input operation received from the operator into an electric signal and outputs the electric signal to the processing circuitry 550. The input interface 530 is implemented by using an input device such as a trackball, a switch button, a mouse, a keyboard, a touchpad for performing an input operation due to the touch with an operation surface, a touch screen in which a display screen and a touchpad are integrated, a non-contact input interface using an optical sensor, or a sound input interface. The input interface 530 may be a control circuitry for a connection interface, or the like, which receives an electronic signal corresponding to an operation from an operation device provided separately from the anonymizing device 50.

The display 540 displays various types of information and various images output from the processing circuitry 550. The display 540 is implemented by using, for example, a display device such as an organic EL monitor, a liquid crystal monitor, a CRT monitor, or a touch panel. For example, the display 540 presents a GUI for receiving an instruction from the operator, various types of display image data, and various processing results by the processing circuitry 550.

The processing circuitry 550 controls each component included in the anonymizing device 50. For example, the processing circuitry 550 is implemented by using a processor. More specifically, the processing circuitry 550 according to the first embodiment includes an acquisition function 551, an anonymization function 552, and an output function 553.

For example, each of the processing functions executed by the acquisition function 551, the anonymization function 552, and the output function 553, which are components of the processing circuitry 550 illustrated in FIG. 9, is stored in the storage circuitry 520 in the form of a program executable by a computer. The processing circuitry 550 is a processor that reads and executes each program from the storage circuitry 520 to implement the function corresponding to each program. In other words, after having read each program, the processing circuitry 550 provides each function illustrated in the processing circuitry 550 of FIG. 9.

All the processing functions, the acquisition function 551, the anonymization function 552, and the output function 553, may be recorded in the storage circuitry 520 in the form of a single program executable by a computer. For example, such a program is also referred to as an anonymization processing program. In this case, the processing circuitry 550 reads the anonymization processing program from the storage circuitry 520 and executes the read anonymization processing program to perform the acquisition function 551, the anonymization function 552, and the output function 553 corresponding to the anonymization processing program.

The acquisition function 551 acquires, from the PACS 40, the medical information in which recipient information and anonymization reference information are set. More specifically, the acquisition function 551 controls the network interface 510 so as to receive the medical information.

The anonymization function 552 is an example of an anonymization processing unit. The anonymization function 552 receives the medical information to which the anonymization reference information is added and anonymizes at least one of the medical image and the supplementary information included in the medical information based on the anonymization reference information added to the medical information. That is, the anonymization function 552 performs an anonymization process to anonymize part of the medical information acquired by the first acquisition function 352 of the anonymizing method setting device 30 based on the anonymization reference information selected by the selection function 353 of the anonymizing method setting device 30. Specifically, the anonymization function 552 anonymizes the medical information acquired by the acquisition function 551 based on the anonymization reference information included in the medical information. More specifically, the anonymization function 552 anonymizes each tag specified by the anonymization reference information by using the method specified by the anonymization reference information. The anonymization function 552 combines the mask data included in the anonymization reference information and the pixel data included in the medical information to anonymize the personal information included in the pixel data.

The output function 553 outputs the anonymized medical information to the recipient indicated by the recipient information. More specifically, the output function 553 controls the network interface 510 so as to transmit the anonymized medical information to the research site 3 via the first network 4.

Figure 10:
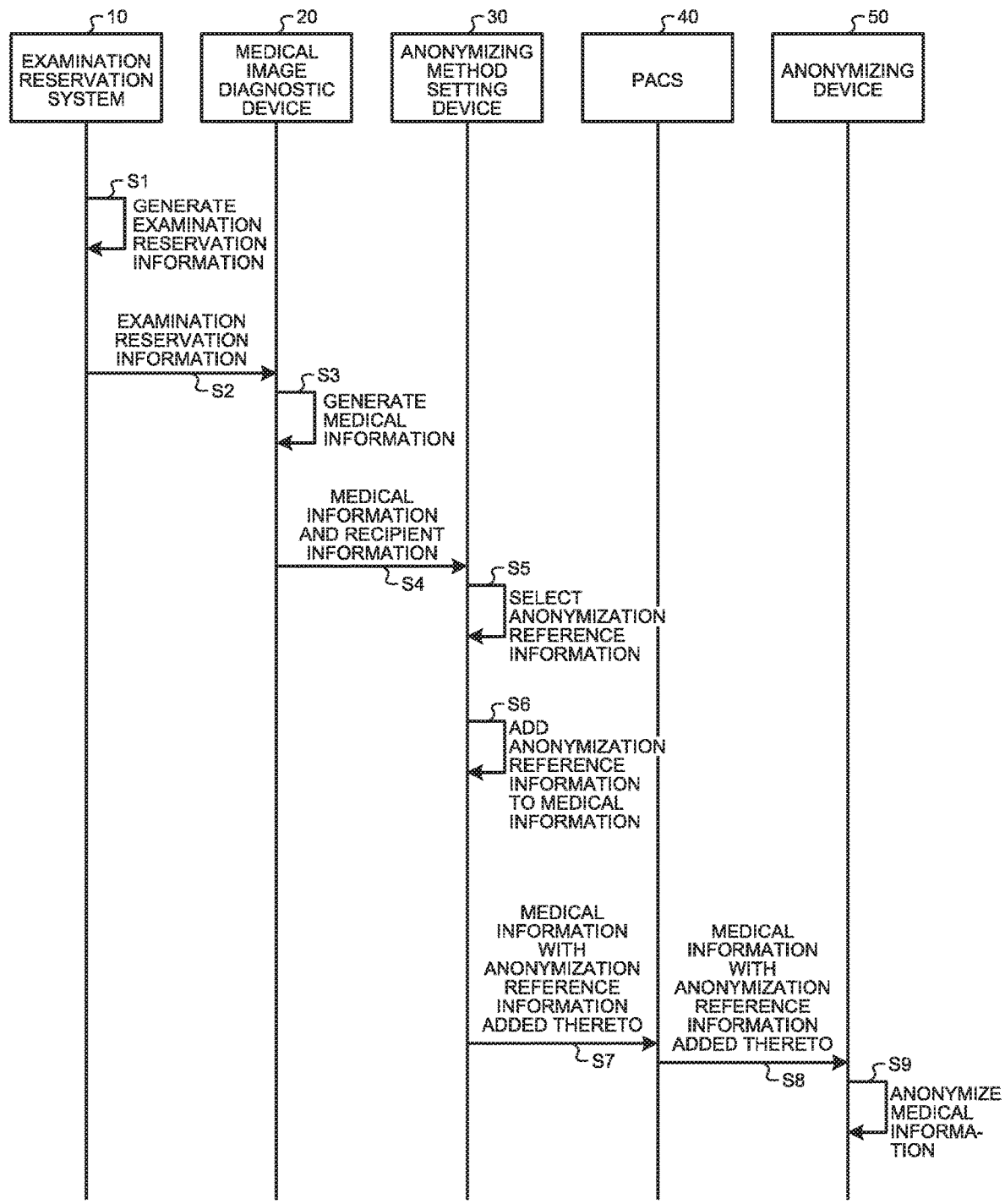
FIG. 10 is a sequence diagram illustrating an example of the procedure of an image generation process according to the first embodiment.

Next, the anonymization process to anonymize medical information according to the first embodiment is described. FIG. 10 is a sequence diagram illustrating an example of the procedure of an image generation process according to the first embodiment.

The examination reservation system 10 generates examination reservation information when an operation of registering provision of the medical information is received (Step S1). The examination reservation system 10 transmits, to the medical image diagnostic device 20, the examination reservation information including the recipient information indicating the recipient of the medical information and the usage purpose of the medical information (Step S2).

The medical image diagnostic device 20 generates medical information based on the examination reservation information transmitted from the examination reservation system 10 (Step S3). The medical image diagnostic device 20 transmits the medical information and the recipient information to the anonymizing method setting device 30 (Step S4).

The selection function 353 of the anonymizing method setting device 30 selects anonymization reference information based on the recipient information received from the medical image diagnostic device 20 (Step S5). The setting function 354 of the anonymizing method setting device 30 adds the selected anonymization reference information to the medical information (Step S6). The output function 355 of the anonymizing method setting device 30 transmits the medical information with the anonymization reference information added thereto to the PACS 40 (Step S7).

The PACS 40 transmits the medical information with the anonymization reference information added thereto to the anonymizing device 50 (Step S8).

The anonymization function 552 of the anonymizing device 50 anonymizes the medical information based on the anonymization reference information added to the medical information (Step S9).

As described above, the medical information anonymizing system 2 terminates the anonymization process.

As described above, with the medical information anonymizing system 2 according to the first embodiment, in the anonymization list information, the recipient information indicating the recipient of the medical information is related to the anonymization reference information indicating the method for anonymizing the medical information. The selection function 353 of the anonymizing method setting device 30 selects the anonymization reference information corresponding to the recipient. The setting function 354 of the anonymizing method setting device 30 adds the selected anonymization reference information to the medical information. The anonymization function 552 of the anonymizing device 50 performs an anonymization process to anonymize personal information, or the like, included in the medical information based on the anonymization reference information added to the medical information. Thus, the medical information anonymizing system 2 according to the first embodiment may anonymize medical information by using the anonymizing method corresponding to the recipient.

Second Embodiment

A second embodiment is described.

Figure 11:
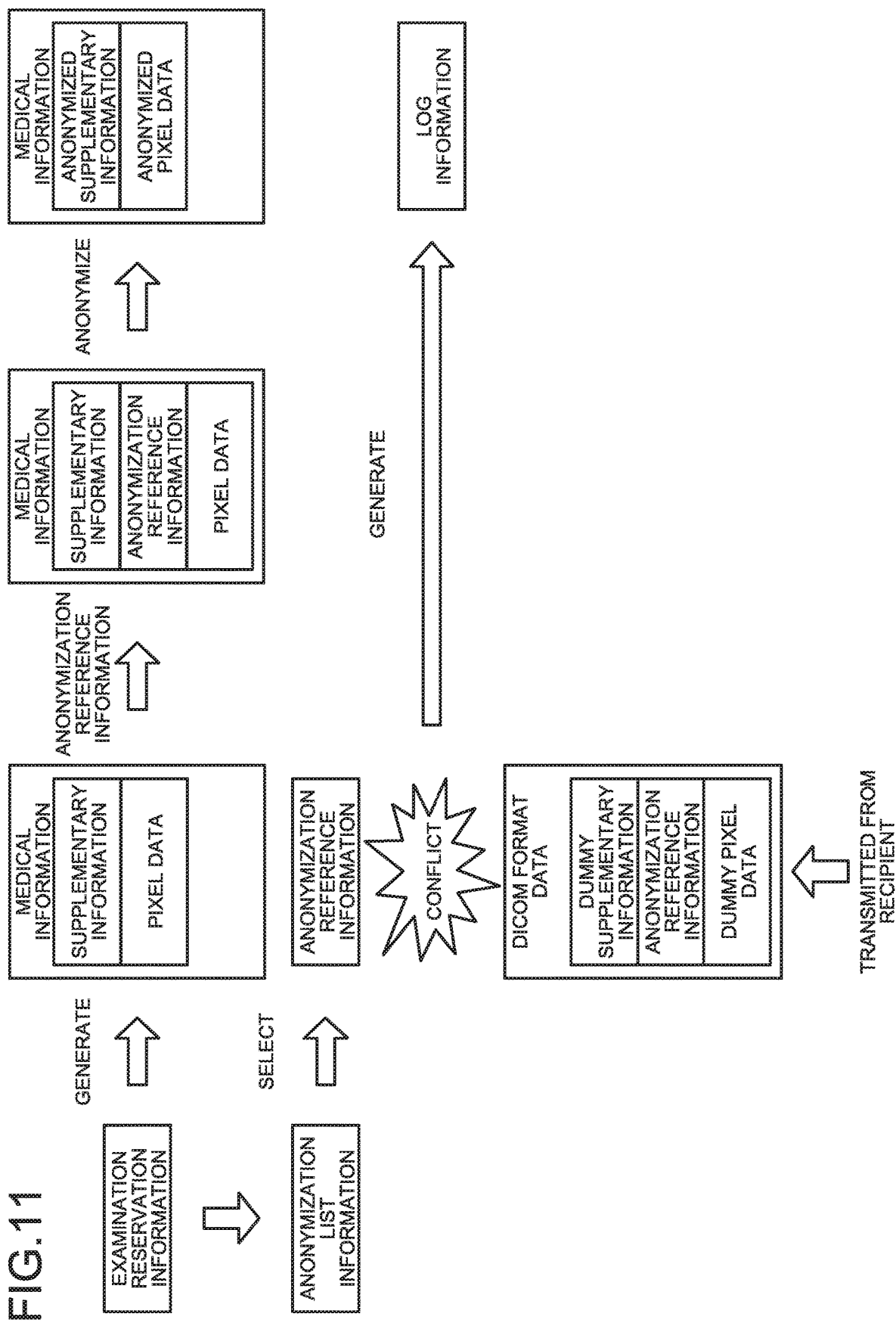
FIG. 11 is a diagram illustrating an example of a medical information anonymizing method according to a second embodiment.

FIG. 11 is a diagram illustrating an example of the method for anonymizing medical information according to the second embodiment. According to the second embodiment, an anonymizing method setting device 30a receives anonymization reference information from the research site 3 that is a recipient.

As illustrated in FIG. 11, the research site 3, which is a recipient, transmits the anonymization reference information indicating the anonymizing method desired by the recipient to the anonymizing method setting device 30a. The research site 3 transmits the data generated in the DICOM format with anonymization reference information added thereto. Specifically, the research site 3 adds the anonymization reference information to the area in which any information in the DICOM format may be written. Dummy supplementary information and dummy pixel data are set in other areas in the DICOM format. The research site 3 transmits the DICOM format data to which the anonymization reference information, the dummy supplementary information, and the dummy pixel data are added.

The anonymization list information stored in the anonymizing method setting device 30a may already include the anonymization reference information on the recipient to which the medical information is transmitted. In this case, there is a possibility that the anonymization reference information transmitted from the research site 3 conflicts with the anonymization reference information in the anonymization list information. Therefore, the anonymizing method setting device 30a determines which anonymization reference information is to be added based on the anonymization strength information described later in FIG. 13. The anonymizing method setting device 30a adds the anonymization reference information to the medical information in accordance with a determination result.

The anonymizing method setting device 30a determines which anonymization reference information is to be added based on the anonymization strength information. That is, the anonymizing device 50 may perform the process to anonymize the medical information by using an anonymizing method different from the anonymizing method in the anonymization reference information transmitted from the recipient. Therefore, it is preferable to notify the recipient that a change has been made to use an anonymizing method different from the anonymizing method in the anonymization reference information transmitted from the recipient. The anonymizing method setting device 30a generates the log information indicating which anonymization reference information has been added, either the anonymization reference information of the research site 3 or the anonymization reference information in the anonymization list information.

Figure 12:
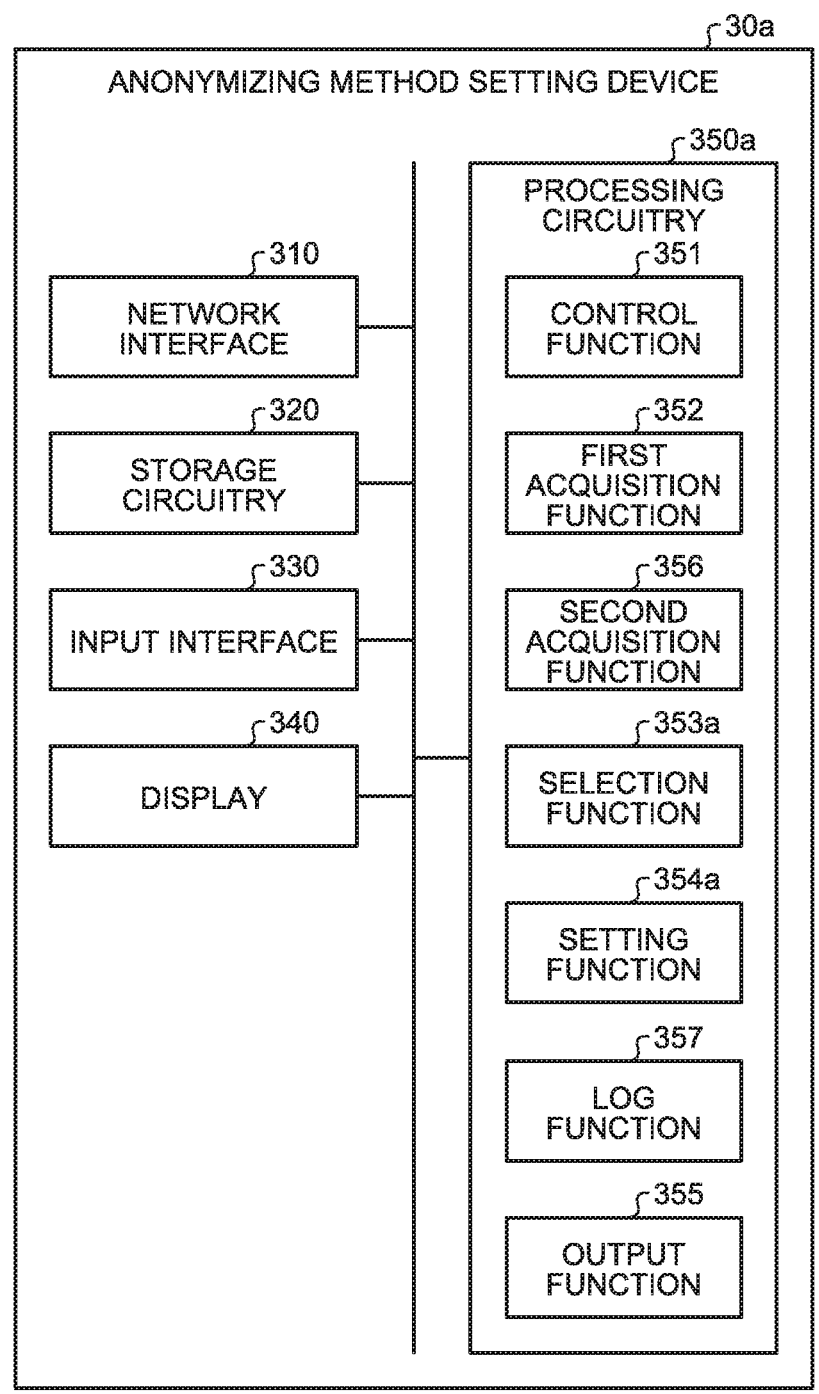
FIG. 12 is a block diagram illustrating an example of the configuration of an anonymizing method setting device according to the second embodiment.

FIG. 12 is a block diagram illustrating an example of the configuration of the anonymizing method setting device 30a according to the second embodiment. A processing circuitry 350a of the anonymizing method setting device 30a according to the second embodiment is different from the anonymizing method setting device 30 according to the first embodiment in that the processing circuitry 350a includes a second acquisition function 356 and a log function 357.

The second acquisition function 356 is an example of a second acquiring unit. The log function 357 is an example of a log unit.

The second acquisition function 356 acquires anonymization reference information from the recipient. More specifically, the second acquisition function 356 acquires the medical information including at least one of a dummy medical image and dummy supplementary information and anonymization reference information. That is, the second acquisition function 356 receives the anonymization reference information generated in the DICOM format. For example, when the second acquisition function 356 receives the DICOM format data to which anonymization reference information, dummy supplementary information, and dummy pixel data are added, the second acquisition function 356 acquires the anonymization reference information from the received data.

A selection function 353a selects anonymization reference information specified by the recipient information from the anonymization list information. When the second acquisition function 356 receives the anonymization reference information from the research site 3, the anonymization list information may already include the anonymization reference information on the recipient. In this case, there is a possibility that the anonymization reference information selected from the anonymization list information conflicts with the anonymization reference information of the second acquisition function 356. Therefore, when the anonymization reference information in the anonymization list information conflicts with the anonymization reference information of the second acquisition function 356, the selection function 353a selects anonymization reference information based on the anonymization strength information.

FIG. 13 is a diagram illustrating an example of the anonymization strength information. The anonymization strength information is information indicating the anonymization strength for each anonymizing method. The anonymization strength is information indicating the strength of anonymization. For example, when the name of a patient is anonymized, the anonymization strength is different in the anonymizing method with which it is possible to determine whether the person is identical and the anonymizing method with which it is not possible to determine whether the person is identical. The anonymizing method with which it is not possible to determine whether the person is identical has high anonymization strength as compared with the anonymizing method with which it is possible to determine whether the person is identical. The anonymization strength is information indicating the above-described anonymization strength. In the case of conflict of anonymization reference information, the selection function 353a selects an anonymizing method having higher anonymization strength. The anonymization strength is, in other words, the information indicating the priority of an anonymizing method. The anonymization strength information illustrated in FIG. 13 indicates that the anonymization strength increases as the numerical value becomes larger.

FIG. 14 is a diagram illustrating an example of the selection of anonymization reference information. When the tags (0010, 0010) are compared with each other, the anonymizing method is "replacement" in the anonymization reference information in the anonymization list information, and the anonymization strength "10" is set in the anonymization strength information in FIG. 13. On the other hand, the anonymizing method is "no anonymization" in the anonymization reference information of the recipient and the anonymization strength "0" is set in the anonymization strength information in FIG. 13. Therefore, the selection function 353a selects "replacement" having higher anonymization strength.

When the tags (0010, 0020) are compared with each other, the anonymizing method is "deletion" in the anonymization reference information of the anonymization list information and the anonymization strength "100" is set in the anonymization strength information of FIG. 13. On the other hand, the anonymizing method is "replacement" in the anonymization reference information of the recipient and the anonymization strength "10" is set in the anonymization strength information of FIG. 13. Thus, the selection function 353a selects "deletion" having higher anonymization strength.

A setting function 354a adds the anonymization reference information acquired by the second acquisition function 356 to the supplementary information in the medical information. More specifically, the setting function 354a sets the anonymizing method selected for each tag by the selection function 353a based on the anonymization strength information in the supplementary information of the medical information. The setting function 354a sets the recipient information in the supplementary information of the medical information.

The log function 357 generates the log information indicating which anonymization reference information has been selected from the anonymization reference information read from the storage circuitry 320 and the anonymization reference information of the second acquisition function 356. That is, the log information is information indicating the anonymizing method selected by the selection function 353a for each tag of the medical information. The log function 357 adds the generated log information to the medical information. For example, the log function 357 writes the log information in the area where any information of the medical information may be written.

The output function 355 transmits, to the PACS 40, the medical information in which the recipient information and the anonymization reference information are set. When the log function 357 generates the log information, the output function 355 transmits the medical information with the log information added thereto.

The anonymization function 552 of the anonymizing device 50 according to the second embodiment performs an anonymization process to anonymize part of the medical information acquired by the first acquisition function 352 of the anonymizing method setting device 30 based on the anonymization reference information selected by the selection function 353 of the anonymizing method setting device 30 as in the first embodiment. Thus, the anonymization function 552 anonymizes part of the medical information based on the anonymization reference information selected by the selection function 353 or the anonymization reference information acquired by the second acquisition function 356. When the anonymization reference information selected from the anonymization list information by the selection function 353 conflicts with the anonymization reference information acquired by the second acquisition function 356, the anonymization function 552 anonymizes part of the medical information by using the anonymizing method selected based on the priority determined for each anonymizing method. Specifically, when the anonymization reference information read from the storage circuitry 320, in which the recipient of the medical information and the anonymization reference information are stored in relation to each other, conflicts with the anonymization reference information acquired by the second acquisition function 356, the anonymization function 552 anonymizes the medical information by using the anonymizing method selected based on the priority determined for each anonymizing method. The output function 553 of the anonymizing device 50 transmits the anonymized medical information and the log information to the research site 3.

Figure 15:
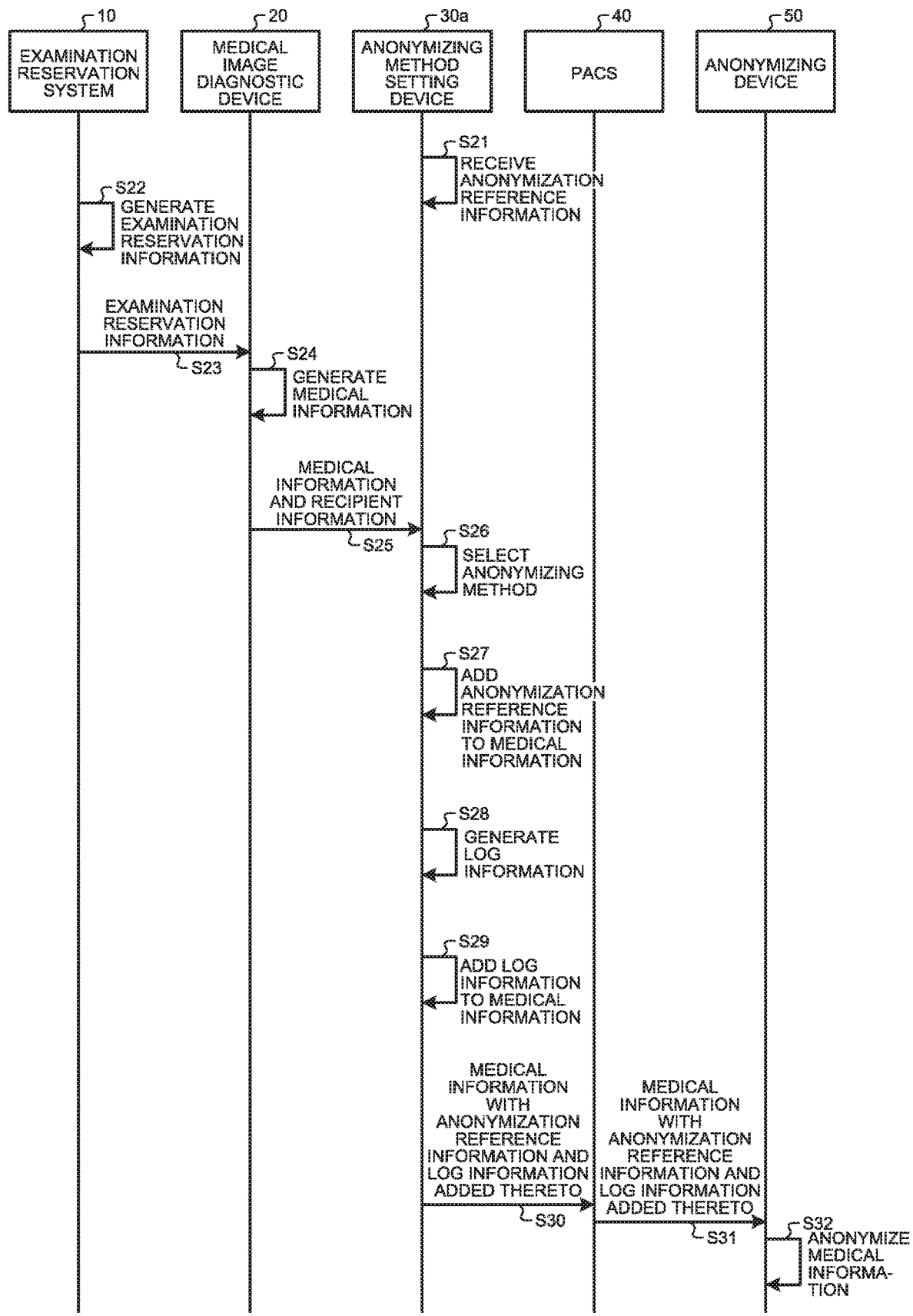
FIG. 15 is a sequence diagram illustrating an example of the procedure of an image generation process according to the second embodiment.

Next, an anonymization process for anonymizing medical information according to the second embodiment is described. FIG. 15 is a sequence diagram illustrating an example of the procedure of an image generation process according to the second embodiment.

The second acquisition function 356 receives the anonymization reference information from the research site 3 (Step S21). The timing for receiving anonymization reference information from the research site 3 may be optionally changed. That is, the second acquisition function 356 may receive the anonymization reference information from the research site 3 after receiving the medical information from the medical image diagnostic device 20 or may receive it at different timing.

The process from Step S22 to Step S25 is the same as the process from Step S1 to Step S4 illustrated in FIG. 10.

The selection function 353a selects the anonymizing method for each tag on the basis of the anonymization reference information in the research site 3 and the anonymization reference information in the anonymization list information based on the anonymization strength information received from the medical image diagnostic device 20 (Step S26).

The setting function 354a adds the anonymizing method for each tag selected by the selection function 353a and the recipient information to the medical information (Step S27).

The log function 357 generates log information (Step S28).

The log function 357 adds the generated log information to the medical information (Step S29).

The output function. 355 transmits, to the PACS 40, the medical information to which the anonymization reference information and the log information have been added (Step S30).

The PACS 40 transmits, to the anonymizing device 50, the medical information to which the anonymization reference information and the log information have been added (Step S31).

The anonymization function 552 of the anonymizing device 50 anonymizes the medical information based on the anonymization reference information added to the medical information (Step S32).

As described above, the medical information anonymizing system 2 terminates the anonymization process.

As described above, with the medical information anonymizing system 2 according to the second embodiment, the second acquisition function 356 of the anonymizing method setting device 30a acquires anonymization reference information from the research site 3. Therefore, the setting function 354a of the anonymizing method setting device 30a may set the anonymizing method specified by the research site 3. Further, in the case of conflict of anonymization reference information, the selection function 353a of the anonymizing method setting device 30a selects the anonymizing method to be set based on the anonymization strength. Thus, the anonymizing method setting device 30a may prevent the anonymization process from being performed by using an anonymizing method with an anonymization strength lower than the anonymization strength expected by a hospital, or the like, which transmits the medical information. The log function 357 of the anonymizing method setting device 30a generates log information. The log function 357 adds the generated log information to the medical information. Thus, the operator or the recipient may know which anonymizing method has been used for anonymization.

Third Embodiment

A third embodiment is described.

Figure 16:
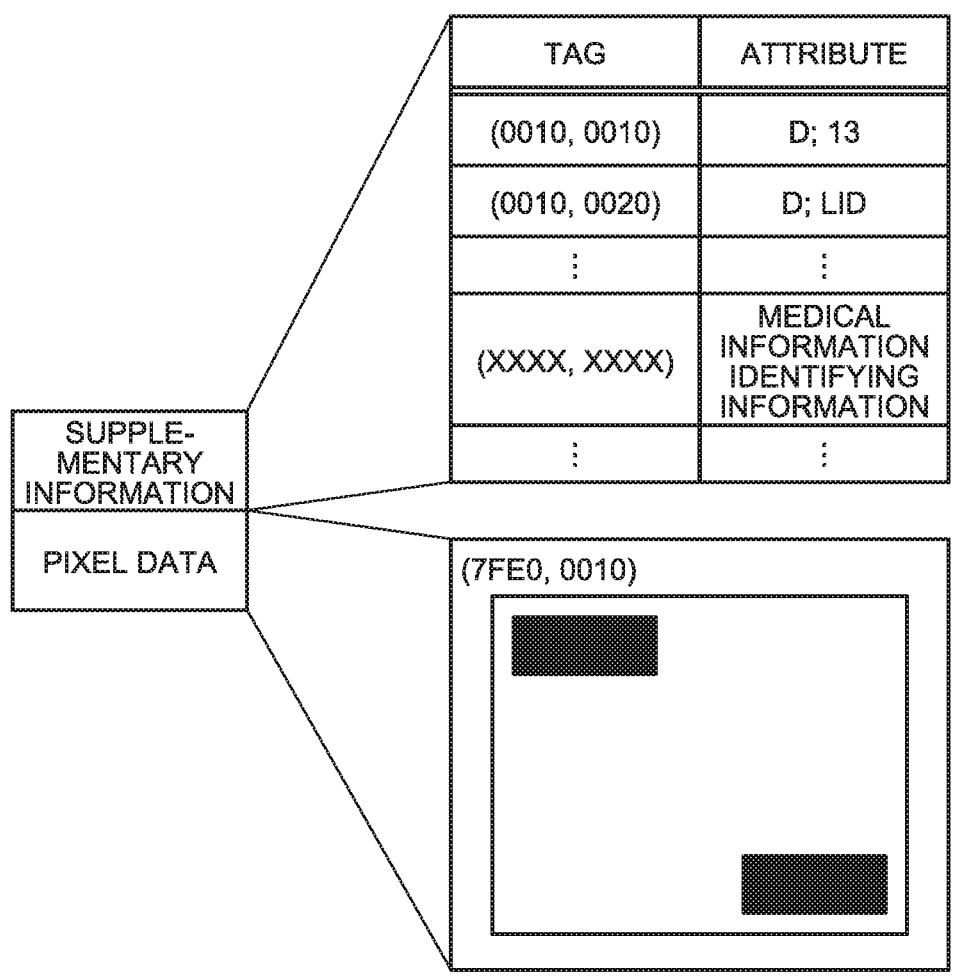
FIG. 16 is a diagram illustrating an example of anonymization reference information according to a third embodiment.

According to the third embodiment, the anonymization reference information is generated in the DICOM format. FIG. 16 is a diagram illustrating an example of the anonymization reference information according to the third embodiment. In the supplementary information of the anonymization reference information, an anonymizing method is set for each tag that is the target to be anonymized. For the pixel data in the anonymization reference information, the mask data for masking the pixel data to be anonymized is set.

In the anonymization reference information according to the third embodiment, any tag includes medical information identifying information. As the anonymization reference information according to the first embodiment is incorporated in the medical information, it is not necessary to identify the medical information to be anonymized. However, as the anonymization reference information according to the third embodiment is not incorporated in the medical information, the medical information identifying information for identifying the medical information to be anonymized is included. The medical information identifying information is, for example, an identification number with which the medical information may be identified. The medical information identifying information is not limited to an identification number and may be the information indicating the area where the medical information is stored or may be other types of information.

For example, when the name of the patient is replaced with numerical value 13, the anonymizing method is described as "D; 13". However, it may be difficult to input alphabets to some tags. In this case, the anonymizing method may be expressed by a numerical value. The value of a specific digit, such as the lower two digits, may represent the anonymizing method. A specific example is given for description; when "18001102" is set in the tag (0010, 0030), "02" which is the lower two digits of "18001102" represents the anonymizing method. In this case, when "02" represents deletion, "180011" is deleted.

Figure 17:
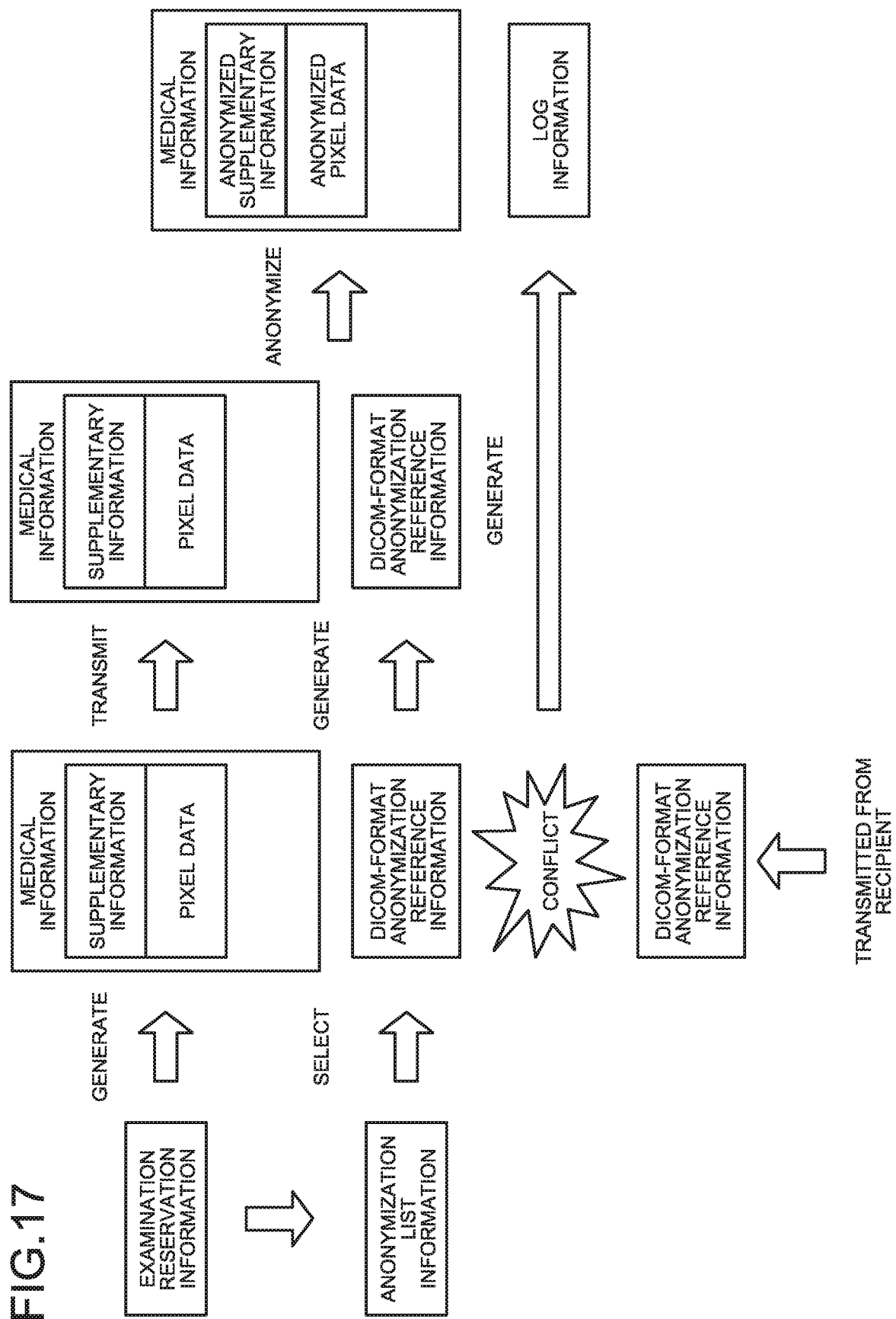
FIG. 17 is a diagram illustrating an example of a medical information anonymizing method according to the third embodiment.

FIG. 17 is a diagram illustrating an example of a medical information anonymizing method according to the third embodiment. According to the third embodiment, the medical image diagnostic device 20 generates the medical information on the subject based on examination reservation information. The medical image diagnostic device 20 transmits the generated medical information to an anonymizing method setting device 30b. According to the third embodiment, as is the case with the second embodiment, the anonymization reference information in the DICOM format may be transmitted from the research site 3 that is a recipient. In the same manner as in the second embodiment, there is a possibility that the anonymization reference information transmitted from the research site 3 conflicts with the anonymization reference information in the anonymization list information. If there is a conflict, it is determined which anonymization reference information is to be added based on the anonymization strength information in the same manner as in the second embodiment. The anonymizing method setting device 30b generates anonymization reference information in the DICOM format based on the determination result when a conflict occurs. The anonymizing method setting device 30b generates the log information indicating which anonymization reference information has been added, either the anonymization reference information of the research site 3 or the anonymization reference information of the anonymization list information. The anonymizing method setting device 30b transmits the medical information generated by the medical image diagnostic device 20 and the generated anonymization reference information in the DICOM format to the anonymizing device 50 via the PACS 40. The anonymizing device 50 anonymizes the received medical information based on the received anonymization reference information.

Figure 18:
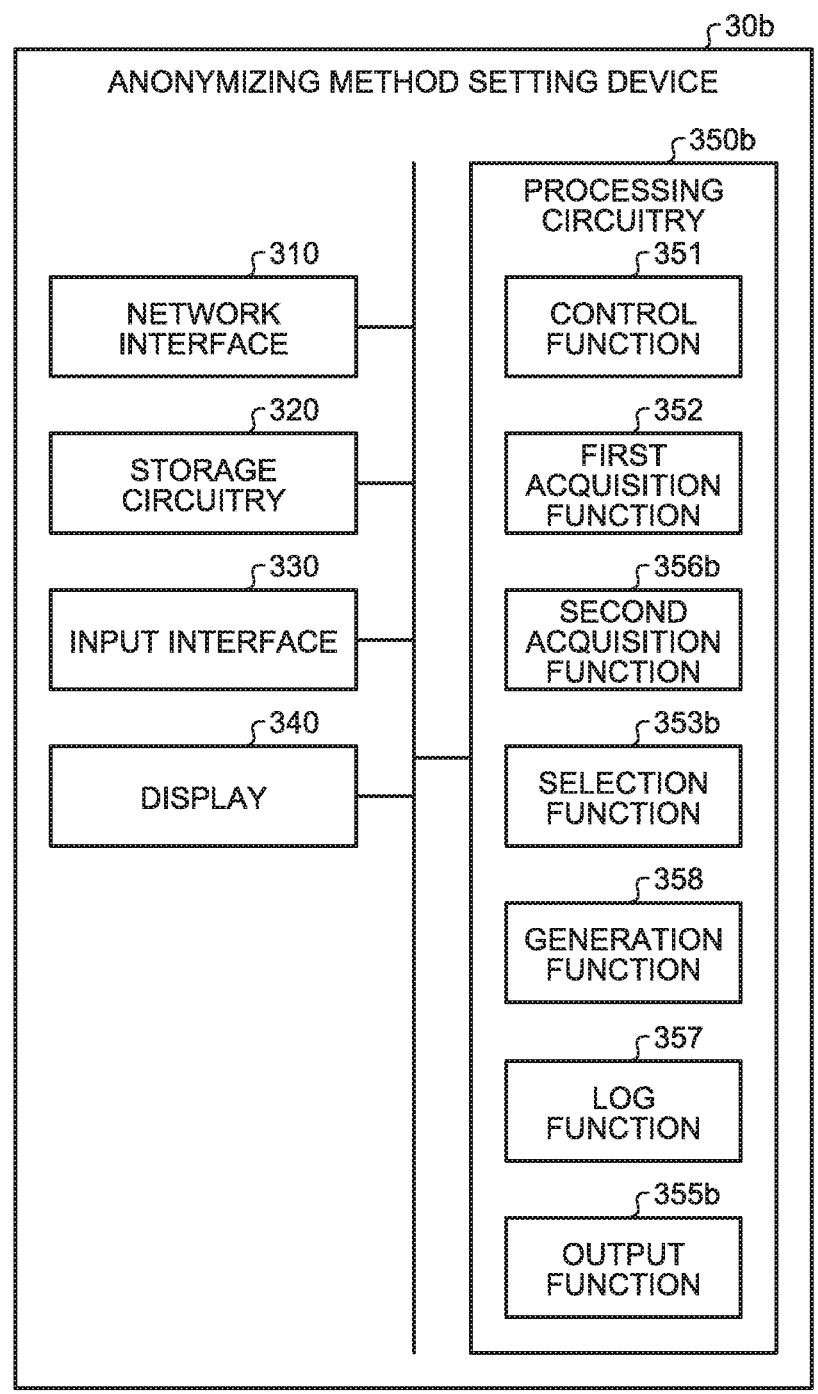
FIG. 18 is a block diagram illustrating an example of the configuration of an anonymizing method setting device according to the third embodiment.

FIG. 18 is a block diagram illustrating an example of the configuration of the anonymizing method setting device 30b according to the third embodiment. A processing circuitry 350b of the anonymizing method setting device 30b according to the third embodiment is different from the processing circuitry 350a of the anonymizing method setting device 30a according to the second embodiment in that the processing circuitry 350b includes a generation function 358 instead of the setting function 354a according to the second embodiment. The anonymization reference information according to the third embodiment is not incorporated in medical information but is independent data in the DICOM format. Therefore, the anonymization reference information according to the third embodiment includes the generation function 358 that generates anonymization reference information instead of the setting function 354a that sets anonymization reference information.

A second acquisition function 356b receives the anonymization reference information generated in the DICOM format from the research site 3. That is, the second acquisition function 356b receives the anonymization reference information in the DICOM format illustrated in FIG. 16.

A selection function 353b selects the anonymization reference information specified by the recipient information for providing the medical information from the anonymization list information in which the recipient information and the DICOM-format anonymization reference information are related to each other. In the same manner as in the second embodiment, when the anonymization reference information of the research site 3 conflicts with the anonymization reference information in the anonymization list information, the selection function 353b selects an anonymizing method for each tag based on anonymization strength information.

The generation function 358 generates anonymization reference information. More specifically, when the anonymization reference information does not conflict, the generation function 358 copies the anonymization reference information selected from the anonymization list information by the selection function 353b to generate anonymization reference information. On the other hand, when the anonymization reference information conflicts, the generation function 358 collects the anonymizing method selected for each tag by the selection function 353b to generate the anonymization reference information.

In the same manner as in the second embodiment, the log function 357 generates log information.

An output function 355b transmits the medical information to be anonymized and the anonymization reference information. When the log function 357 generates log information, the output function 355b transmits the medical information to be anonymized, the anonymization reference information, and the log information.

The anonymization function 552 of the anonymizing device 50 according to the third embodiment performs an anonymization process to anonymize part of the medical information based on the anonymization reference information transmitted from the anonymizing method setting device 30 in the same manner as in the first embodiment. The output function 553 of the anonymizing device 50 transmits the anonymized medical information and the log information to the research site 3.

Figure 19:
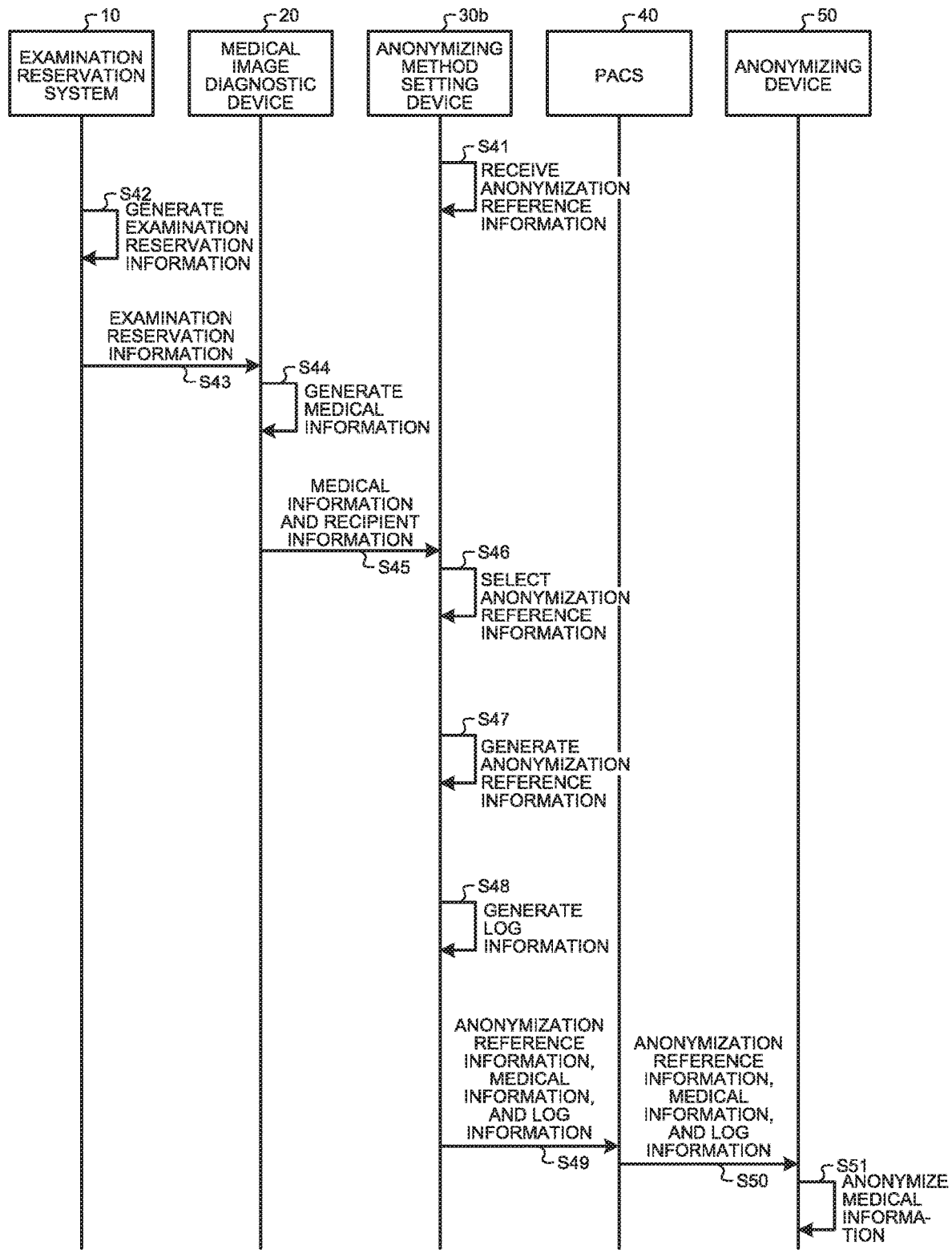
FIG. 19 is a sequence diagram illustrating an example of the procedure of an anonymization process according to the third embodiment.

Next, the anonymization process for anonymizing medical information according to the third embodiment is described. FIG. 19 is a sequence diagram illustrating an example of the procedure of the anonymization process according to the third embodiment.

The second acquisition function 356b receives the anonymization reference information generated in the DICOM format from the research site 3 (Step S41).

The process from Step S42 to Step S45 is the same as the process from Step S1 to Step S4 illustrated in FIG. 10.

The selection function 353 of the anonymizing method setting device 30 selects the anonymization reference information in the DICOM format based on the recipient information received from the medical image diagnostic device 20 (Step S46).

The generation function 358 generates anonymization reference information (Step S47).

The log function 357 generates log information (Step S48).

The output function 355b transmits the medical information to be anonymized, the anonymization reference information, and the log information to the PACS 40 (Step S49).

The PACS 40 transmits the medical information to be anonymized, the anonymization reference information, and the log information to the anonymizing device 50 (Step S50).

The anonymization function 552 of the anonymizing device 50 anonymizes the medical information based on the received anonymization reference information (Step S51).

Thus, the medical information anonymizing system 2 terminates the anonymization process.

As described above, with the medical information anonymizing system 2 according to the third embodiment, the anonymization reference information is generated in the DICOM format. Therefore, the anonymizing method setting device 30b may receive the anonymization reference information from the research site 3 without a newly provided route for transmitting and receiving the anonymization reference information.

In the description according to the third embodiment, the anonymizing method setting device 30b includes the second acquisition function 356b, the generation function 358, and the log function 357. However, the anonymizing device 50 may include the second acquisition function 356b, the generation function 358, and the log function 357. In this case, the anonymizing method setting device 30b transmits the anonymization reference information selected by the selection function 353b to the anonymizing device 50 via the PACS 40. The anonymizing device 50 acquires the anonymization reference information from the research site 3. When the anonymization reference information received from the anonymizing method setting device 30b conflicts with the anonymization reference information acquired from the research site 3, the anonymizing device 50 selects an anonymizing method for each tag based on the anonymization strength information and generates anonymization reference information. The anonymizing device 50 anonymizes the medical information based on the generated anonymization reference information.

Fourth Embodiment

A fourth embodiment is described.

According to the fourth embodiment, the medical information including anonymization reference information is provided to the research site 3 that is a recipient. When the medical information does not include the anonymization reference information, the recipient is not able to know what anonymization process has been performed on the supplementary information and the pixel data included in the medical information. Therefore, according to the fourth embodiment, the medical information including the anonymization reference information used for an anonymization process is provided to the research site 3.

Figure 20:
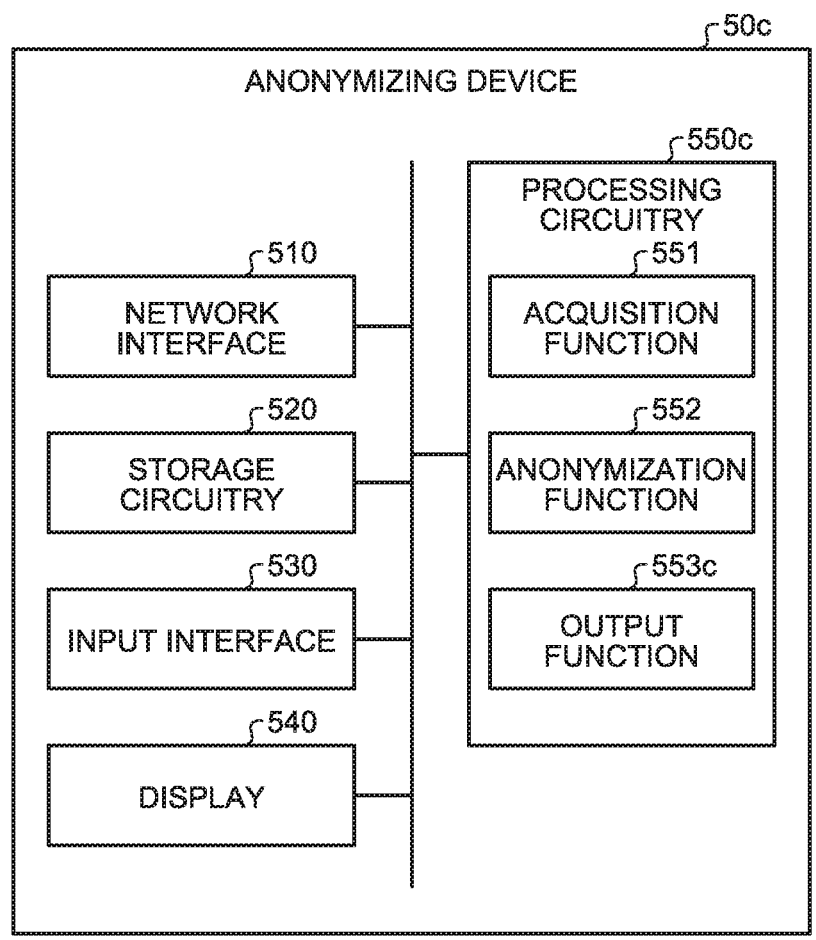
FIG. 20 is a block diagram illustrating an example of the configuration of an anonymizing device according to a fourth embodiment.

FIG. 20 is a block diagram illustrating an example of the configuration of an anonymizing device 50c according to the fourth embodiment. An output function 553c of a processing circuitry 550c of the anonymizing device 50c according to the fourth embodiment outputs the medical information including the anonymization reference information used for anonymization by the anonymization function 552. That is, the output function 553c transmits the medical information including the anonymization reference information to the research site 3.

The output format of anonymization reference information by the output function 553c is not limited. For example, the output function 553c may output the anonymization reference information incorporated in the supplementary information. Specifically, the output function 553c may add the anonymization reference information to a standard tag or a private tag of the supplementary information.

The anonymizing device 50c according to the fourth embodiment is applicable to the first embodiment, the second embodiment, and the third embodiment.

The anonymizing method setting device 30a according to the second embodiment acquires the DICOM format data from the research site 3 as illustrated in FIG. 11. The anonymizing method setting device 30a adds the anonymization reference information included in the DICOM format data to the medical information. Accordingly, the anonymizing device 50 uses the anonymization reference information included in the DICOM format data to anonymize the medical information. In such a case, the output function 553c outputs the medical information including the anonymization reference information.

As the anonymizing method setting device 30a according to the second embodiment acquires the anonymization reference information from the research site 3, the anonymization reference information acquired from the research site 3 may conflict with the anonymization reference information selected from the anonymization list information. Therefore, the log function 357 according to the second embodiment generates the log information indicating which anonymization reference information has been added, either the anonymization reference information of the research site 3 or the anonymization reference information in the anonymization list information. When the log function 357 generates the log information, the output function 355 according to the second embodiment outputs the medical information to which the log information has been added. This allows the research site 3 to known which anonymization reference information has been used and what anonymization has been performed.

Figure 21:
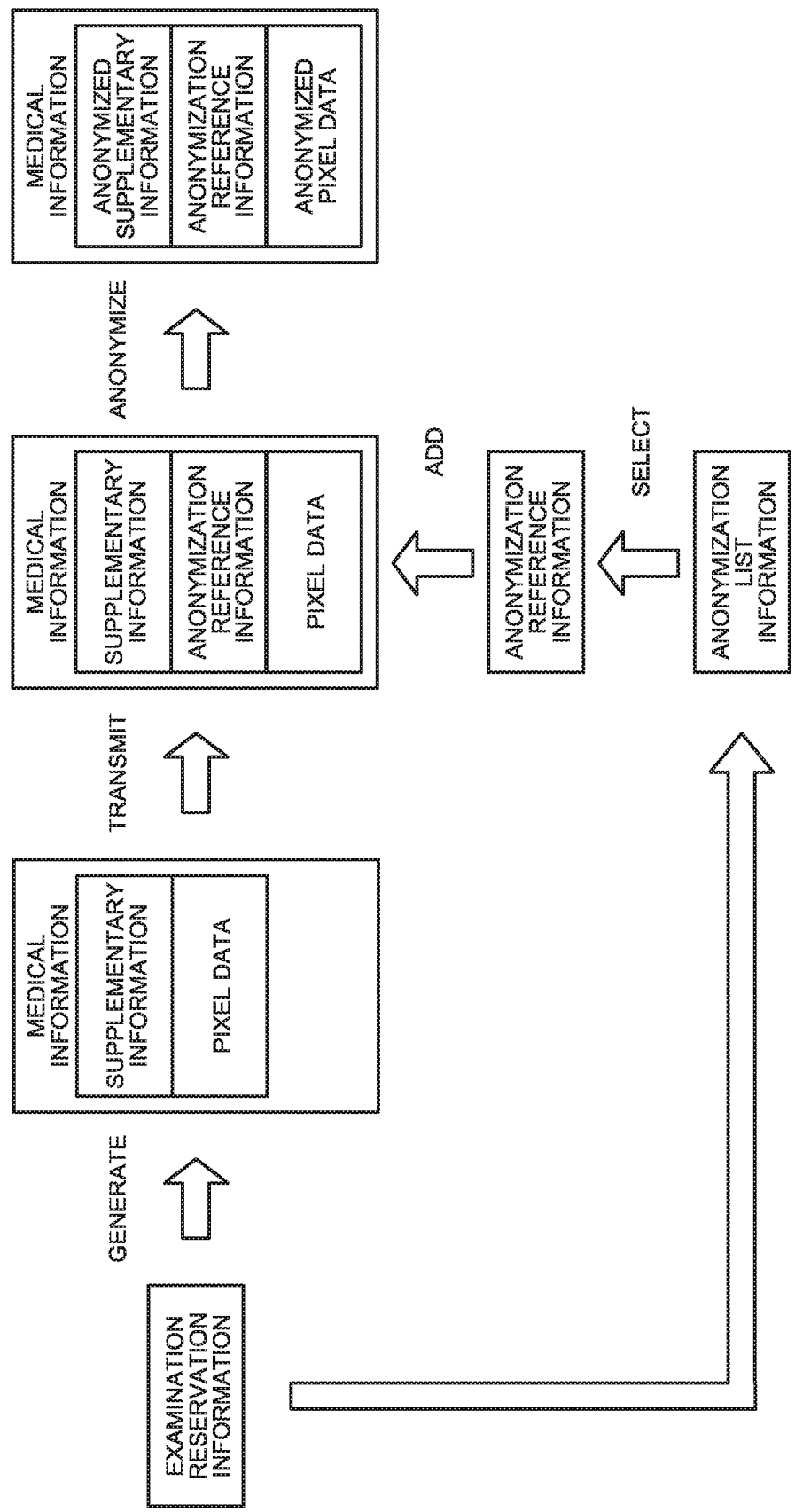
FIG. 21 is a diagram illustrating an example of a medical information anonymizing method according to the fourth embodiment.

FIG. 21 is a diagram illustrating an example of a medical information anonymizing method according to the fourth embodiment. The examination reservation system 10 generates examination reservation information when the examination reservation by the medical image diagnostic device 20 is received. The medical image diagnostic device 20 generates the medical information on the subject based on the examination reservation information. The anonymizing method setting device 30 selects anonymization reference information from the anonymization list information. The anonymizing method setting device 30 adds the selected anonymization reference information to the medical information generated by the medical image diagnostic device 20. The anonymizing device 50c generates the medical information in which at least one of the supplementary information and the pixel data is anonymized based on the anonymization reference information added to the medical information. The anonymizing device 50c outputs the anonymization reference information used for the anonymization and the anonymized medical information to the research site 3.

As described above, with the medical information anonymizing system 2 according to the fourth embodiment, the output function 553c of the anonymizing device 50c outputs the anonymization reference information used for anonymization by the anonymization function 552 and the medical information including at least one of the medical image and the supplementary information anonymized by the anonymization function 552. That is, the output function 553c transmits the anonymization reference information and the medical information to the research site 3. Thus, the medical information anonymizing system 2 allows the recipient of the medical information to know the method for anonymizing the medical information.

Fifth Embodiment

A fifth embodiment is described.

According to the fifth embodiment, when the subject such as a patient gives his/her consent, an anonymization process is performed. The consent according to the fifth embodiment is the consent to the disclosure of medical information.

Figure 22:
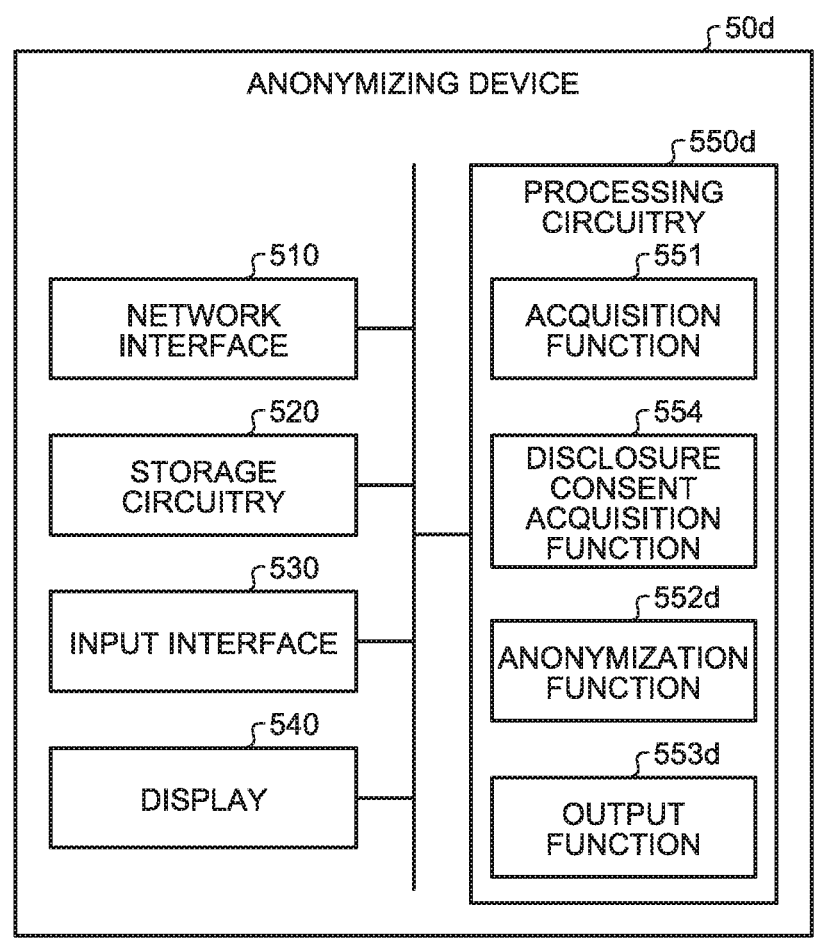
FIG. 22 is a block diagram illustrating an example of the configuration of an anonymizing device according to a fifth embodiment.

FIG. 22 is a block diagram illustrating an example of the configuration of an anonymizing device 50d according to the fifth embodiment. A processing circuitry 550d of the anonymizing device 50d is different from the anonymizing device 50 according to the first embodiment in that the processing circuitry 550d includes a disclosure consent acquisition function 554.

The disclosure consent acquisition function 554 acquires the input indicating the consent to the disclosure of the medical information from the subject such as a patient. For example, when the medical staff, such as a doctor, presses the button indicating the consent to the disclosure of the medical information in the terminal operated, the disclosure consent acquisition function 554 acquires the disclosure consent information indicating the consent to the disclosure of the medical information from the terminal.

For example, the terminal operated by the medical staff displays a disclosure confirmation screen for confirming the consent to the disclosure of the medical information. The terminal receives the operation of pressing the button indicating the consent to the disclosure of the medical information among the buttons included in the disclosure confirmation screen. The terminal transmits disclosure consent information when the button indicating the consent to the disclosure of the medical information is pressed. The disclosure consent acquisition function 554 receives the disclosure consent information transmitted from the terminal. Thus, the disclosure consent acquisition function 554 acquires the disclosure consent information.

The input indicating the consent to the disclosure of the medical information is not limited to the pressing of the button but may be the input of a password owned by the subject, the input of the signature of the subject written on the touch panel, the input of scanned data on the consent form indicating the consent to the disclosure of the medical information, or the combination thereof. The disclosure consent acquisition function 554 may acquire the disclosure consent information from not only the terminal operated by the medical staff but also the terminal operated by the subject or may acquire the disclosure consent information from a reading device that scans the consent form.

An anonymization function 552d anonymizes at least one of the medical image and the supplementary information included in the medical information based on the anonymization reference information added to the medical information if the consent from the subject has been acquired. More specifically, the anonymization function 552d enables the disclosure flag, which is the flag indicating whether the subject such as a patient has given consent to the disclosure, if the disclosure consent acquisition function 554 has acquired the disclosure consent information. On the other hand, if the disclosure consent acquisition function 554 has not acquired the disclosure consent information, the anonymization function 552d continuously disables the disclosure flag. In order to provide the medical information, the anonymization function 552d anonymizes the medical information based on the anonymization reference information if the disclosure flag is valid. On the other hand, the anonymization function 552d does not anonymize the medical information if the disclosure flag is invalid.

The recipient information and the anonymization reference information are related to each other in the anonymization list information. The recipient information indicates the recipient and the usage purpose. The disclosure consent acquisition function 554 may acquire the input indicating the consent to the disclosure of the medical information from the subject for each recipient and each purpose of use.

The disclosure consent acquisition function 554 may acquire the input indicating the consent to the disclosure for each tag of the supplementary information and pixel data. Accordingly, the anonymization function 552d anonymizes the tag of the supplementary information and the pixel data for which the subject has given consent. An output function 553d outputs the medical information including the tag of the supplementary information and the pixel data anonymized by the anonymization function 552d. That is, the output function 553d does not output the tag of the supplementary information and the pixel data for which the subject has not given consent to the disclosure. This allows the subject to designate the disclosure target.

The output function 553d transmits, to the research site 3, the anonymization reference information used for anonymization by the anonymization function 552d and the medical information anonymized by the anonymization function 552d. That is, when the disclosure consent acquisition function 554 has not acquired the input indicating the consent to the disclosure of the medical information from the subject, the output function 553d does not transmit the medical information. The output function 553d may transmit the medical information instead of both the anonymization reference information and the medical information.

The anonymizing device 50d according to the fifth embodiment is applicable to the first embodiment, the second embodiment, and the third embodiment.

Figure 23:
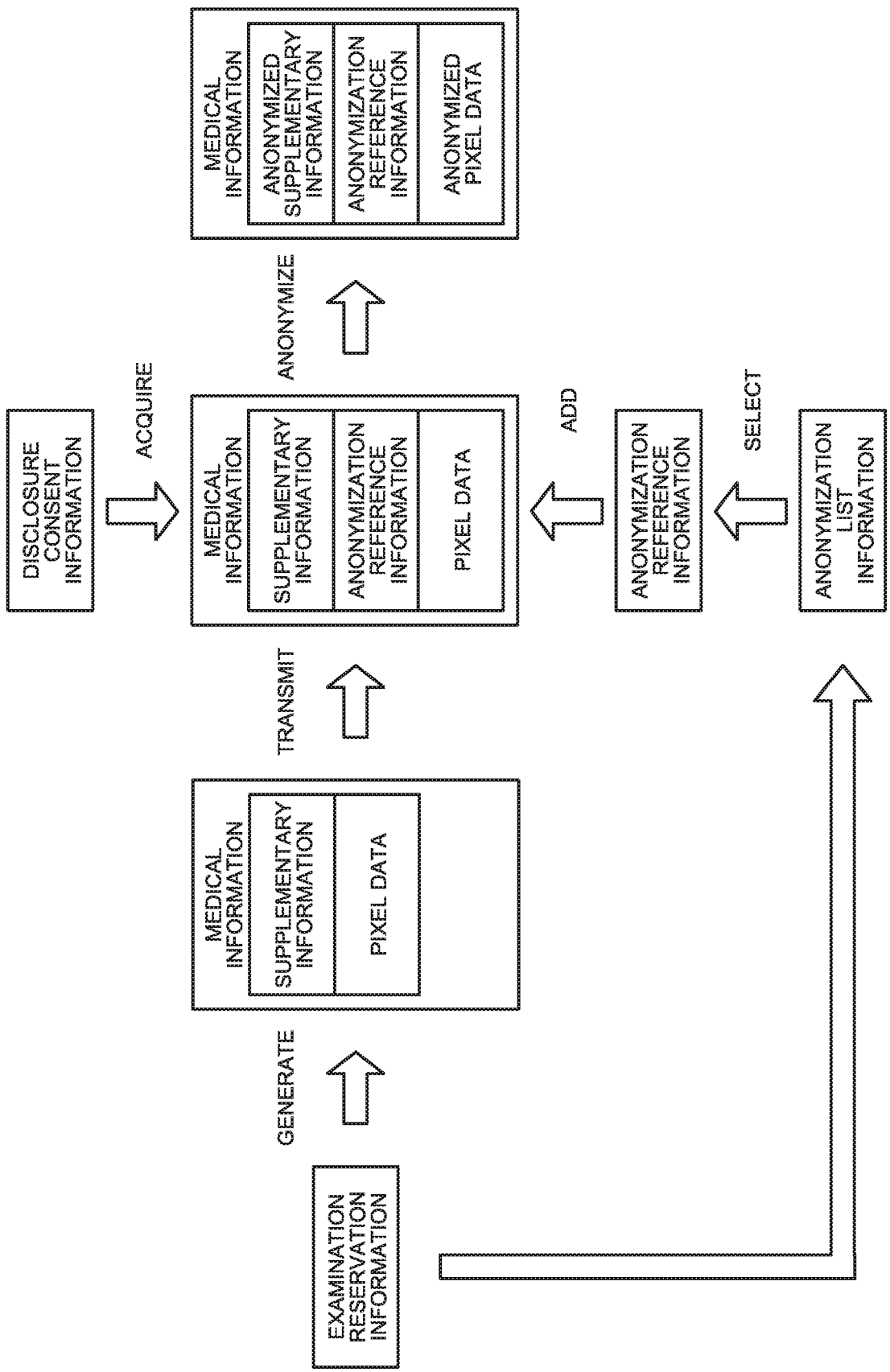
FIG. 23 is a diagram illustrating an example of a medical information anonymizing method according to the fifth embodiment.

FIG. 23 is a diagram illustrating an example of a medical information anonymizing method according to the fifth embodiment. The examination reservation system 10 generates examination reservation information when the examination reservation by the medical image diagnostic device 20 is received. The medical image diagnostic device 20 generates the medical information on the subject based on the examination reservation information. The anonymizing method setting device 30 selects anonymization reference information from the anonymization list information. The anonymizing method setting device 30 adds the selected anonymization reference information to the medical information generated by the medical image diagnostic device 20. When the subject such as a patient has given consent to the disclosure of the anonymized medical information, the anonymizing device 50d acquires the disclosure consent information indicating the consent to the anonymization of the medical information. When the disclosure consent information has been acquired, the anonymizing device 50d anonymizes at least one of the supplementary information and the pixel data in the medical information based on the anonymization reference information added to the medical information. On the other hand, when the disclosure consent information has not been acquired, the anonymizing device 50d does not anonymize the medical information because the subject has not given consent. The anonymizing device 50d does not also provide the corresponding medical information.

As described above, with the medical information anonymizing system 2 according to the fifth embodiment, the disclosure consent acquisition function 554 of the anonymizing device 50d acquires the input indicating the consent to the disclosure of the medical information from the subject. The anonymization function 552d anonymizes at least one of the medical image and the supplementary information included in the medical information based on the anonymization reference information added to the medical information if the disclosure consent acquisition function 554 has acquired the consent. The output function 553d outputs the medical information to the research site 3 if the anonymization function 552d has anonymized the medical information. On the other hand, the output function 553d does not output the medical information to the research site 3 when the anonymization function 552d has not anonymized the medical information. Thus, the medical information anonymizing system 2 may disclose the medical information to the research site 3 if the subject such as a patient has given consent to the disclosure of the medical information.

Sixth Embodiment

A sixth embodiment is described.

According to the sixth embodiment, an anonymization process is performed when the subject such as a patient has given consent. The consent according to the sixth embodiment is the consent to the anonymization of medical information.

Figure 24:
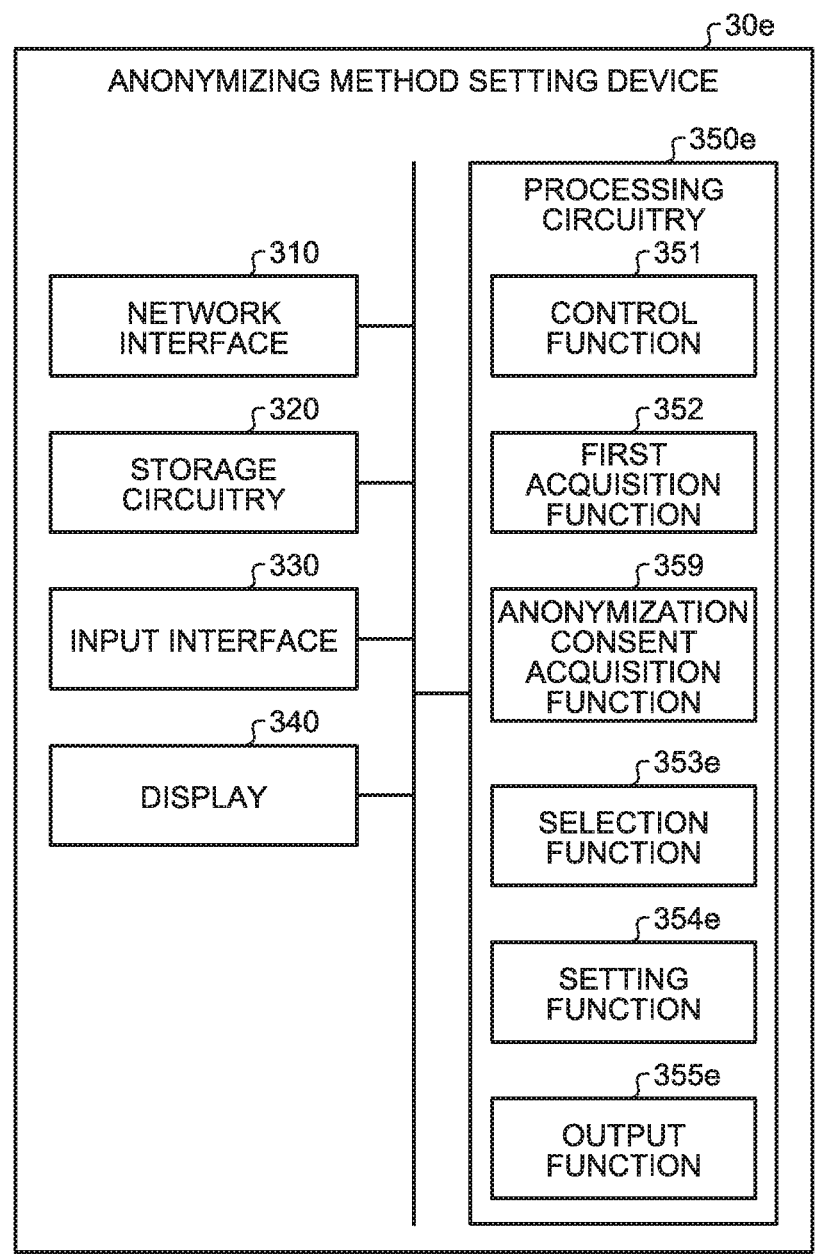
FIG. 24 is a block diagram illustrating an example of the configuration of an anonymizing method setting device according to a sixth embodiment.

FIG. 24 is a block diagram illustrating an example of the configuration of an anonymizing method setting device 30e according to the sixth embodiment. A processing circuitry 350e of the anonymizing method setting device 30e is different from the anonymizing method setting device 30 according to the first embodiment in that the processing circuitry 350e includes an anonymization consent acquisition function 359.

The anonymization consent acquisition function 359 acquires the input indicating the consent to the anonymization of medical information from the subject such as a patient. For example, when the medical staff such as a doctor presses the button indicating the consent to the anonymization of the medical information in the terminal operated, the anonymization consent acquisition function 359 acquires the anonymization consent information indicating the consent to the anonymization of the medical information from the terminal.

For example, the terminal operated by the medical staff displays an anonymization confirmation screen for confirming the consent to the anonymization of medical information. The terminal receives the operation of pressing the button indicating the consent to the anonymization of the medical information among the buttons included in the anonymization confirmation screen. The terminal transmits the anonymization consent information when the button indicating the consent to the anonymization of the medical information is pressed. The anonymization consent acquisition function 359 receives the anonymization consent information transmitted from the terminal. Thus, the anonymization consent acquisition function 359 acquires the anonymization consent information. The anonymization consent acquisition function 359 enables the anonymization flag, which is the flag indicating whether the subject such as a patient has given consent to the anonymization, if the anonymization consent information has been acquired. On the other hand, the anonymization consent acquisition function 359 continuously disables the anonymization flag if the anonymization consent information has not been acquired.

The input indicating the consent to the anonymization of the medical information is not limited to the pressing of the button but may be the input of a password owned by the subject, the input of the signature of the subject written on the touch panel, the input of scanned data on the consent form indicating the consent to the anonymization of the medical information, or the combination thereof. The anonymization consent acquisition function 359 may acquire the anonymization consent information from not only the terminal operated by the medical staff but also the terminal operated by the subject or may acquire the anonymization consent information from the reading device that scans a consent form.

A selection function 353e selects the anonymization reference information from the anonymization list information if the anonymization flag is valid. On the other hand, if the anonymization flag is invalid, the selection function 353e does not select the anonymization reference information from the anonymization list information.

A setting function 354e adds the anonymization reference information to the supplementary information in the medical information if the consent has been received from the subject. Specifically, if the anonymization flag is valid, the setting function 354e sets the recipient information and the anonymization reference information selected by the selection function 353 in the area where any information in the medical information generated in the DICOM format may be written. That is, if the anonymization flag is invalid, the selection function 353e does not select the anonymization reference information from the anonymization list information, and therefore the setting function 354e does not set the recipient information and the anonymization reference information.

If the anonymization flag is valid, an output function 355e outputs, to the PACS 40, the medical information in which recipient information and the anonymization reference information are set. That is, when the anonymization flag is invalid, the output function 355e does not output the medical information.

The anonymizing method setting device 30e according to the sixth embodiment is applicable to the first embodiment, the second embodiment, and the third embodiment.

The selection function 353a of the anonymizing method setting device 30a according to the second embodiment selects the anonymizing method to be set based on the anonymization strength. The anonymization consent acquisition function 359 may acquire the lower limit value of the anonymization strength. In this case, based on the anonymization strength information, the setting function 354e determines whether the anonymization strength of the anonymizing method for each tag indicated in the anonymization reference information is equal to or more than the lower limit value.

If the anonymization strength is equal to or more than the lower limit value, the setting function 354e sets the recipient information and the anonymization reference information selected by the selection function 353e in the area where any information in the medical information generated in the DICOM format may be written. Conversely, if the anonymization strength is less than the lower limit value, the setting function 354e does not set the recipient information and the anonymization reference information selected by the selection function 353e. Thus, the output function 355e outputs the medical information in which the anonymization reference information having the anonymization strength specified by the subject is set. This allows the setting function 354e to prevent the disclosure with less than the anonymization strength specified by the subject.

The selection function 353e may determine whether the anonymization strength of the anonymizing method for each tag indicated in the anonymization reference information is equal to or more than the lower limit value. In this case, based on the anonymization strength information, the selection function 353e determines whether the anonymization strength of the anonymizing method indicated by the anonymization reference information to be selected from the anonymization list information is equal to or more than to the lower limit value acquired by the anonymization consent acquisition function 359. If the anonymization strength of the anonymizing method indicated by the anonymization reference information to be selected is equal to or more than the lower limit value, the selection function 353e selects the corresponding anonymization reference information.

Conversely, if the anonymization strength of the anonymizing method indicated by the anonymization reference information to be selected is less than the lower limit value, the selection function 353e may change the anonymizing method indicated by the anonymization reference information to an anonymizing method that is equal to or more than the lower limit value. The selection function 353e selects the anonymization reference information including the changed anonymizing method. The setting function 354e sets the anonymization reference information selected by the selection function 353e. Then, the output function 355e outputs the medical information in which the anonymization reference information having the anonymization strength designated by the subject is set. Thus, the selection function 353e may prevent the anonymized medical information from being unable to be provided to the research site 3 while the anonymization strength designated by the subject is ensured.

Figure 25:
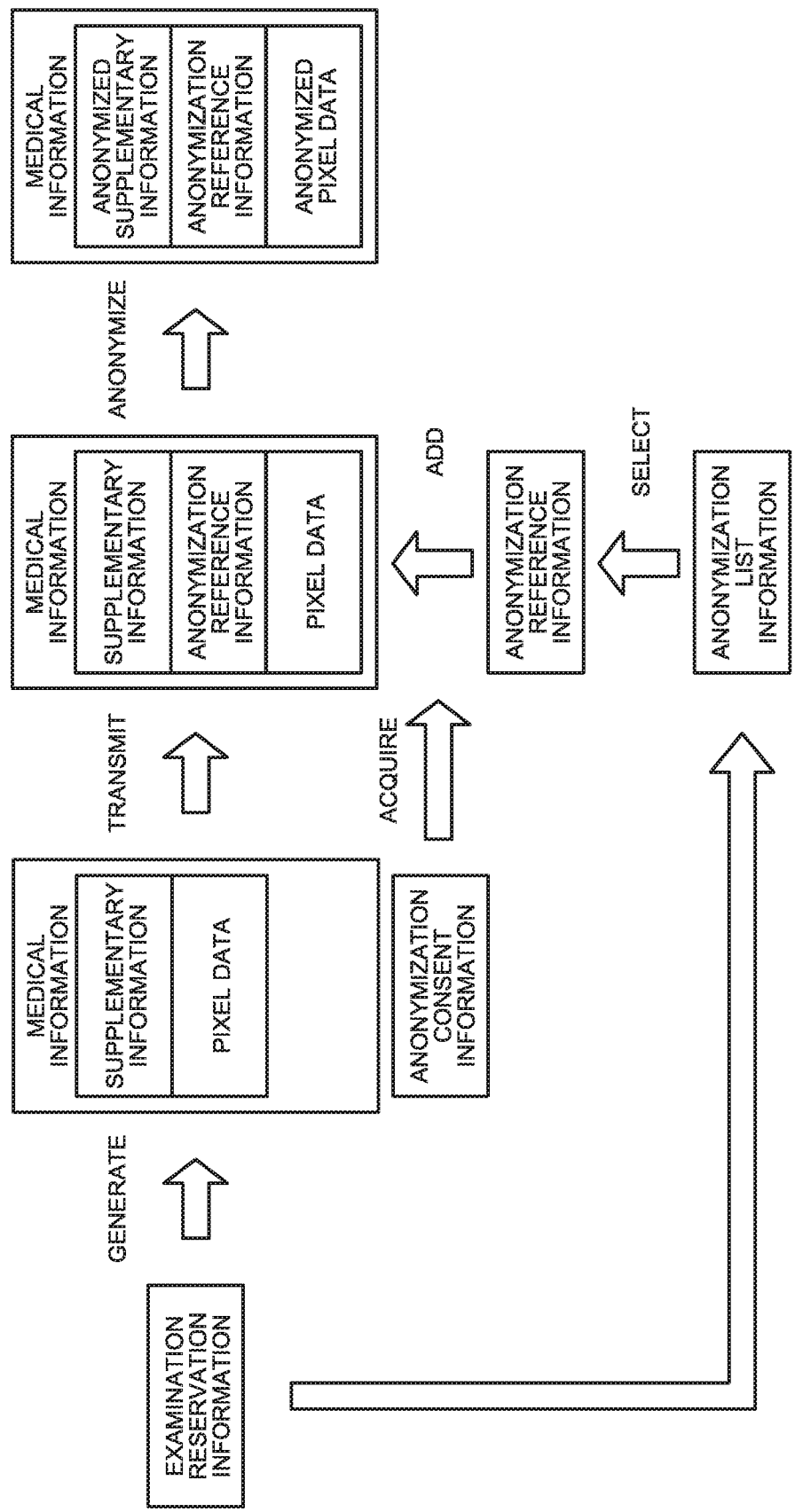
FIG. 25 is a diagram illustrating an example of a medical information anonymizing method according to the sixth embodiment.

FIG. 25 is a diagram illustrating an example of the medical information anonymizing method according to the sixth embodiment. The examination reservation system 10 generates examination reservation information when the examination reservation by the medical image diagnostic device 20 is received. The medical image diagnostic device 20 generates the medical information on the subject based on the examination reservation information. When the subject such as a patient has given consent to the anonymization of the medical information, the anonymizing method setting device 30e acquires the anonymization consent information indicating the consent to the anonymization of the medical information. When the anonymization consent information is acquired, the anonymizing method setting device 30e adds the anonymization reference information to the supplementary information in the medical information. The anonymizing method setting device 30e outputs, to the anonymizing device 50, the medical information to which the anonymization consent information has been added. When the medical information with the anonymization reference information added thereto is acquired, the anonymizing device 50 anonymizes at least one of the supplementary information and the pixel data in the medical information. Conversely, when the anonymization consent information has not been acquired, the anonymizing method setting device 30e does not add the anonymization reference information. Furthermore, the anonymizing method setting device 30e does not output the medical information to the anonymizing device 50. That is, the anonymizing device 50 also does not provide the medical information.

As described above, with the medical information anonymizing system 2 according to the sixth embodiment, the anonymization consent acquisition function 359 of the anonymizing method setting device 30e may acquire the input indicating the consent to the anonymization of the medical information from the subject such as a patient. The setting function 354e adds the anonymization reference information to the supplementary information in the medical information if the anonymization consent acquisition function 359 has received the consent. The output function 355e outputs, to the PACS 40, the medical information with the anonymization reference information added thereto if the setting function 354e has added the anonymization reference information to the supplementary information in the medical information. The anonymizing device 50 acquires the medical information with the anonymization reference information added thereto from the PACS 40 and anonymizes the anonymization reference information. The anonymizing device 50 outputs the anonymized medical information to the research site 3. Conversely, the output function 355e does not output the medical information to the PACS 40 if the setting function 354e has not added the anonymization reference information to the medical information. That is, the medical information anonymizing system 2 does not output the medical information to the research site 3. Thus, the medical information anonymizing system 2 may disclose the medical information to the research site 3 if the subject such as a patient has given consent to the anonymization of the medical information.

According to the above-described embodiment, the medical information anonymizing system 2 includes the independent anonymizing method setting device 30, 30a, 30b, or 30e. However, all or a part of the functions provided in the anonymizing method setting devices 30, 30a, 30b, and 30e may be provided in the medical image diagnostic device 20 or the PACS 40.

In the example of the case described according to the above embodiment, each processing function is performed by a single processing circuitry (the processing circuitries 350, 350a, 350b, 350e, 550, 550c, and 550d); however, the embodiments are not limited thereto. For example, the processing circuitries 350, 350a, 350b, 350e, 550, 550c, and 550d may be configured by combining a plurality of independent processors so that each processor may execute each program to perform each processing function. Processing functions provided in the processing circuitries 350, 350a, 350b, 350e, 550, 550c, and 550d may be performed by being distributed or integrated in a single or a plurality of processing circuitries as appropriate.

The term "processor" used in the description of each of the above-described embodiments refers to, for example, a CPU (central processing unit), a GPU (graphics processing unit), or a circuit such as an application specific integrated circuit (ASIC), or a programmable logic device (e.g., a simple programmable logic device (SPLD), a complex programmable logic device (CPLD), and a field programmable gate array (FPGA)). A configuration may be such that, instead of storing a program in a memory, the program may be directly installed in a circuitry of the processor. In this case, the processor reads and executes a program installed in the circuitry to perform a function. Each processor according to the present embodiment may be configured as a single circuitry but also as a single processor combining a plurality of independent circuitries to perform its function.

A program executed by the processor is provided by being previously installed in a ROM (read only memory), a storage unit, or the like. The program may be provided by being recorded in a computer-readable storage medium, such as a CD (compact disk)-ROM, FD (flexible disk), CD-R (recordable), or DVD (digital versatile disk), in the form of file installable or executable in these devices. The program may be stored in a computer connected via a network such as the Internet and may be provided or distributed by being downloaded via the network. For example, the program is configured as a module including each functional unit. As the actual hardware, the CPU reads and executes a program from a storage medium such as a ROM so that each module is loaded in the primary storage device and generated in the primary storage device.

Each component of each device illustrated is a functional concept and does not necessarily need to be physically configured as illustrated. That is, the specific form of separation/integration of each device is not limited to the one illustrated, and all or part thereof may be functionally or physically separated/integrated in any unit in accordance with various loads and usage conditions. All or any part of the processing functions performed by the devices may be implemented by a CPU and a program analyzed and executed by the CPU or may be implemented as wired logic hardware.

The medical image processing method described in the above embodiment may be implemented when a computer such as a personal computer or a workstation executes a prepared program. The program may be distributed via a network such as the Internet. The program may be recorded in a computer-readable recording medium such as a hard disk, a flexible disk (FD), a CD-ROM, an MO, or a DVD and may be read from the recording medium by the computer to be executed.

According to at least one of the embodiments described above, it is possible to anonymize medical information by using an anonymizing method that is different for each piece of medical information.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information anonymizing system, comprising:
an anonymizing method setting device comprising first processing circuitry; and
an anonymizing device comprising second processing circuitry,
wherein the first processing circuitry is configured to
acquire medical information generated in a format based on a communication standard for a medical image and including a medical image and supplementary information,
select anonymization reference information related to a recipient of medical information from anonymization list information that includes recipient information and anonymization reference information in relation to each other, the recipient information representing recipients of the medical information, the anonymization reference information representing anonymizing methods for anonymizing the medical information, and
add the selected anonymization reference information to the medical information, and
the second processing circuitry is configured to
receive the medical information, and, based on the anonymization reference information added to the medical information, anonymize the medical information, and
transmit the medical information having components including the anonymized medical image, the anonymized supplementary information, and the anonymization reference information to the recipient of the medical information.

2. The medical information anonymizing system according to claim 1, wherein the first processing circuitry is further configured to add the anonymization reference information to the medical information, if consent has been acquired from a subject.

3. The medical information anonymizing system according to claim 1, wherein the second processing circuitry is further configured to anonymize the medical information based on the anonymization reference information added to the medical information, if consent has been acquired from a subject.

4. The medical information anonymizing system according to claim 1, wherein the first processing circuitry is further configured to add the anonymization reference information to the medical information, if consent to anonymization of the medical information has been acquired from a subject.

5. The medical information anonymizing system according to claim 1, wherein the second processing circuitry is further configured to anonymize the medical information based on the anonymization reference information added to the medical information, if consent to disclosure of the medical information has been acquired from a subject.

6. The medical information anonymizing system according to claim 1, wherein
the anonymization list information further includes usage purposes of the medical information in relation to the recipient information and the anonymization reference information, and
the first processing circuitry is further configured to select the anonymization reference information related to the recipient and a usage purpose of the medical information from the anonymization list information and add the selected anonymization reference information to the medical information.

7. The medical information anonymizing system according to claim 1, wherein the first processing circuitry is further configured to
perform a communication with a digital imaging and communications in medicine (DICOM) standard as a communication standard for the medical image, and
add the anonymization reference information to a private tag or a standard tag based on the DICOM standard.

8. The medical information anonymizing system according to claim 1, wherein the first processing circuitry is further configured to
acquire the anonymization reference information from a recipient, and
add the acquired anonymization reference information to the medical information.

9. The medical information anonymizing system according to claim 8, wherein the first processing circuitry is further configured to acquire medical information including a dummy medical image, dummy supplementary information, and the anonymization reference information.

10. The medical information anonymizing system according to claim 8, wherein the first processing circuitry is further configured to receive the anonymization reference information generated in the DICOM format.

11. The medical information anonymizing system according to claim 8, wherein when the anonymization reference information acquired from the recipient conflicts with the anonymization reference information selected from the anonymization list information, the second processing circuitry is further configured to anonymize the medical information by using a selected one of the anonymizing methods based on a priority determined for each anonymizing method.

12. The medical information anonymizing system according to claim 11, wherein the first processing circuitry is further configured to generate log information indicating which one of the anonymization reference information selected from the anonymization list information and the anonymization reference information acquired from the recipient has been selected.

13. The medical information anonymizing system according to claim 1, wherein the first processing circuitry is further configured to display a specification screen for specifying an anonymization target when the anonymizing method indicated by the anonymization reference information has a setting such that the anonymization target is specified by an operator.

14. The medical information anonymizing system according to claim 13, wherein the first processing circuitry is further configured to
store the anonymization target specified on the specification screen, and
when the medical information includes information identical to the stored anonymization target, display the specification screen in which the information identical to the anonymization target is specified as the anonymization target.

\* \* \* \* \*